United States Patent
Nguyen et al.

(10) Patent No.: US 8,936,631 B2
(45) Date of Patent: Jan. 20, 2015

(54) APPARATUS AND METHODS FOR TREATING HOLLOW ANATOMICAL STRUCTURES

(75) Inventors: Hoa D. Nguyen, San Jose, CA (US); Arthur W. Zikorus, San Jose, CA (US); Stephen W. Lee, San Jose, CA (US)

(73) Assignee: Covidien LP, Mansfield, MA (US)

( * ) Notice: Subject to any disclaimer, the term of this patent is extended or adjusted under 35 U.S.C. 154(b) by 595 days.

(21) Appl. No.: 12/860,761

(22) Filed: Aug. 20, 2010

(65) Prior Publication Data

US 2011/0166519 A1    Jul. 7, 2011

Related U.S. Application Data

(60) Provisional application No. 61/292,112, filed on Jan. 4, 2010, provisional application No. 61/357,907, filed on Jun. 23, 2010.

(51) Int. Cl.
| | |
|---|---|
| *A61F 7/12* | (2006.01) |
| *A61F 7/00* | (2006.01) |
| *A61B 18/04* | (2006.01) |
| *A61N 1/40* | (2006.01) |
| *A61B 18/08* | (2006.01) |

(52) U.S. Cl.
CPC .............. *A61N 1/403* (2013.01); *A61B 18/082* (2013.01)
USPC ................................ 607/113; 607/96; 606/29

(58) Field of Classification Search
USPC .................................. 606/27–45; 607/96, 113
See application file for complete search history.

(56) References Cited

U.S. PATENT DOCUMENTS

| | | | |
|---|---|---|---|
| 373,399 | A | 11/1887 | Hamilton |
| 452,220 | A | 5/1891 | Gunning |
| 833,759 | A | 10/1906 | Sourwine |
| 1,943,543 | A | 1/1934 | McFadden |
| 2,022,065 | A | 11/1935 | Wappler er al. |

(Continued)

FOREIGN PATENT DOCUMENTS

| | | |
|---|---|---|
| CN | 1068525 | 3/2000 |
| JP | 02-104348 | 4/1990 |
| WO | WO 98/09575 | 3/1998 |

OTHER PUBLICATIONS

Aaron, Electrofulguration for Varicose Veins, The Medical Letter on Drugs and Therapeutics, Jul. 12, 1968, vol. 10, No. 14, Issue 248, p. 54.

(Continued)

*Primary Examiner* — Linda Dvorak
*Assistant Examiner* — Adam Avigan
(74) *Attorney, Agent, or Firm* — Thomas M. Johnston, Esq.

(57) ABSTRACT

A method of performing therapy on tissue using a medical apparatus. The apparatus includes a shaft configured for insertion into a hollow anatomical structure (HAS) and has a tissue sensor and a therapeutic energy application device both located on the shaft. The method comprises: receiving electrical power at a first power level and directing the first-level power to the tissue sensor and not to the therapeutic energy application device, thereby enabling tissue sensing with the tissue sensor; receiving electrical power at a second power level higher than the first-level power; and, in response to receipt of the second-level power, directing the second-level power to the therapeutic energy application device, thereby enabling performance of therapy on the tissue with the therapeutic energy application device. Additional methods and apparatus are disclosed as well.

11 Claims, 18 Drawing Sheets

(56) References Cited

U.S. PATENT DOCUMENTS

| | | |
|---|---|---|
| 3,100,489 A | 8/1963 | Bagley |
| 3,230,957 A | 1/1966 | Seifert |
| 3,301,258 A | 1/1967 | Werner |
| 3,313,293 A | 4/1967 | Chesebrough |
| 3,667,476 A * | 6/1972 | Muller .................. 607/96 |
| 3,920,021 A | 11/1975 | Hiltebrandt |
| 4,034,762 A | 7/1977 | Cosens et al. |
| 4,481,953 A | 11/1984 | Gold et al. |
| 4,532,924 A | 8/1985 | Auth et al. |
| 4,548,207 A | 10/1985 | Reimels |
| 4,561,445 A | 12/1985 | Berke et al. |
| 4,643,186 A | 2/1987 | Rosen et al. |
| 4,674,499 A | 6/1987 | Pao |
| 4,682,596 A | 7/1987 | Bales et al. |
| 4,765,331 A | 8/1988 | Petruzzi et al. |
| 4,832,051 A | 5/1989 | Jarvik et al. |
| 4,966,597 A | 10/1990 | Cosman |
| 4,998,933 A | 3/1991 | Eggers et al. |
| 5,122,137 A * | 6/1992 | Lennox .................. 606/40 |
| 5,281,216 A | 1/1994 | Klicek |
| 5,281,218 A | 1/1994 | Imran |
| 5,330,470 A | 7/1994 | Hagen |
| 5,334,193 A | 8/1994 | Nardella |
| 5,403,311 A | 4/1995 | Abele et al. |
| 5,437,664 A | 8/1995 | Cohen et al. |
| 5,458,596 A | 10/1995 | Lax et al. |
| 5,556,396 A | 9/1996 | Cohen et al. |
| 5,562,703 A | 10/1996 | Desai |
| 5,630,426 A | 5/1997 | Eggers et al. |
| 5,643,257 A | 7/1997 | Cohen et al. |
| 5,658,282 A | 8/1997 | Daw et al. |
| 5,693,952 A * | 12/1997 | Cox .................. 250/551 |
| 5,695,495 A | 12/1997 | Ellman et al. |
| 5,700,262 A | 12/1997 | Acosta et al. |
| 5,709,224 A | 1/1998 | Behl et al. |
| 5,734,903 A | 3/1998 | Saulpaugh et al. |
| 5,743,903 A | 4/1998 | Stern et al. |
| 5,752,951 A | 5/1998 | Yanik |
| 5,766,167 A | 6/1998 | Eggers et al. |
| 5,810,802 A | 9/1998 | Panescu et al. |
| 5,868,744 A | 2/1999 | Willmen |
| 5,893,849 A | 4/1999 | Weaver |
| 5,897,553 A | 4/1999 | Mulier et al. |
| 5,925,045 A | 7/1999 | Reimels et al. |
| 5,928,159 A | 7/1999 | Eggers et al. |
| 5,954,715 A | 9/1999 | Harrington et al. |
| 5,964,754 A | 10/1999 | Osypka |
| 5,976,131 A | 11/1999 | Guglielmi et al. |
| 6,003,397 A | 12/1999 | Yasuhira |
| 6,004,319 A | 12/1999 | Goble et al. |
| 6,014,589 A | 1/2000 | Farley et al. |
| 6,030,382 A | 2/2000 | Fleischman et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,679 A | 3/2000 | Slater et al. |
| 6,042,590 A | 3/2000 | Sporri et al. |
| 6,066,136 A | 5/2000 | Geistert |
| 6,071,277 A | 6/2000 | Farley et al. |
| 6,077,261 A | 6/2000 | Behl et al. |
| 6,090,104 A | 7/2000 | Webster, Jr. |
| 6,106,524 A | 8/2000 | Eggers et al. |
| 6,113,596 A | 9/2000 | Hooven et al. |
| 6,123,702 A | 9/2000 | Swanson et al. |
| 6,135,997 A | 10/2000 | Laufer et al. |
| 6,139,527 A | 10/2000 | Laufer et al. |
| 6,152,899 A | 11/2000 | Farley et al. |
| 6,156,032 A | 12/2000 | Lennox |
| 6,165,172 A | 12/2000 | Farley et al. |
| 6,170,832 B1 | 1/2001 | Ernst |
| 6,176,856 B1 * | 1/2001 | Jandak et al. .................. 606/29 |
| 6,183,468 B1 | 2/2001 | Swanson et al. |
| 6,200,312 B1 | 3/2001 | Zikorus et al. |
| 6,228,082 B1 | 5/2001 | Baker et al. |
| 6,237,606 B1 | 5/2001 | Zikorus et al. |
| 6,238,393 B1 | 5/2001 | Mulier et al. |
| 6,258,084 B1 | 7/2001 | Goldman et al. |
| 6,263,248 B1 | 7/2001 | Farley et al. |
| 6,267,758 B1 | 7/2001 | Daw et al. |
| 6,283,961 B1 | 9/2001 | Underwood et al. |
| 6,293,944 B1 | 9/2001 | Ellman et al. |
| 6,304,776 B1 | 10/2001 | Muntermann |
| 6,312,428 B1 | 11/2001 | Eggers et al. |
| 6,322,559 B1 | 11/2001 | Daulton et al. |
| 6,332,880 B1 | 12/2001 | Yang et al. |
| 6,346,102 B1 | 2/2002 | Harrington et al. |
| 6,353,763 B1 | 3/2002 | George et al. |
| 6,379,349 B1 | 4/2002 | Müller et al. |
| 6,391,026 B1 | 5/2002 | Hung et al. |
| 6,398,777 B1 | 6/2002 | Navarro et al. |
| 6,398,780 B1 | 6/2002 | Farley et al. |
| 6,401,719 B1 | 6/2002 | Farley et al. |
| 6,451,011 B2 | 9/2002 | Tu |
| 6,480,746 B1 | 11/2002 | Ingle et al. |
| 6,488,679 B1 | 12/2002 | Swanson et al. |
| 6,539,265 B2 | 3/2003 | Medhkour et al. |
| 6,565,557 B1 | 5/2003 | Sporri et al. |
| 6,587,731 B1 | 7/2003 | Ingle et al. |
| 6,613,045 B1 | 9/2003 | Laufer et al. |
| 6,638,273 B1 | 10/2003 | Farley et al. |
| 6,669,692 B1 | 12/2003 | Nelson et al. |
| 6,682,526 B1 | 1/2004 | Jones et al. |
| 6,689,126 B1 | 2/2004 | Farley et al. |
| 6,712,840 B2 | 3/2004 | Sun |
| 6,723,094 B1 | 4/2004 | Desinger |
| 6,726,684 B1 | 4/2004 | Woloszko et al. |
| 6,733,499 B2 | 5/2004 | Scheib |
| 6,752,767 B2 | 6/2004 | Turovskiy et al. |
| 6,752,803 B2 | 6/2004 | Goldman et al. |
| 6,761,718 B2 | 7/2004 | Madsen |
| 6,769,433 B2 | 8/2004 | Zikorus et al. |
| 6,770,070 B1 | 8/2004 | Balbierz |
| 6,969,388 B2 | 11/2005 | Goldman et al. |
| 6,981,972 B1 | 1/2006 | Farley et al. |
| 7,004,942 B2 | 2/2006 | Laird et al. |
| 7,041,098 B2 | 5/2006 | Farley et al. |
| 7,160,289 B2 | 1/2007 | Cohen |
| 7,195,630 B2 | 3/2007 | Ciarrocca |
| 7,396,355 B2 | 7/2008 | Goldman et al. |
| 7,517,349 B2 | 4/2009 | Truckai et al. |
| 7,620,453 B1 * | 11/2009 | Propato et al. .................. 607/37 |
| 7,625,372 B2 | 12/2009 | Esch et al. |
| 7,641,633 B2 | 1/2010 | Laufer et al. |
| 7,824,408 B2 | 11/2010 | Mirizzi et al. |
| 8,055,357 B2 * | 11/2011 | Swanson .................. 607/130 |
| 2001/0023365 A1 | 9/2001 | Medhkour et al. |
| 2001/0041888 A1 | 11/2001 | Goldman et al. |
| 2002/0072744 A1 | 6/2002 | Harrington et al. |
| 2002/0128641 A1 | 9/2002 | Underwood et al. |
| 2002/0143325 A1 | 10/2002 | Sampson et al. |
| 2002/0148476 A1 | 10/2002 | Farley et al. |
| 2003/0191512 A1 | 10/2003 | Laufer et al. |
| 2004/0153053 A1 | 8/2004 | Ishikawa |
| 2004/0176761 A1 | 9/2004 | Desinger |
| 2005/0043761 A1 | 2/2005 | Connelly et al. |
| 2005/0070894 A1 | 3/2005 | McClurken |
| 2005/0234443 A1 | 10/2005 | Rioux et al. |
| 2006/0030849 A1 | 2/2006 | Mirizzi et al. |
| 2006/0085054 A1 * | 4/2006 | Zikorus et al. .................. 607/96 |
| 2006/0189979 A1 | 8/2006 | Esch et al. |
| 2006/0217692 A1 | 9/2006 | Neuberger |
| 2008/0039829 A1 | 2/2008 | Goldman et al. |
| 2008/0243076 A1 | 10/2008 | Goldan et al. |
| 2009/0149909 A1 | 6/2009 | Ameri |
| 2009/0281535 A1 | 11/2009 | Truckai et al. |
| 2009/0312673 A1 | 12/2009 | Thapliyal et al. |
| 2011/0166518 A1 | 7/2011 | Nguyen et al. |

OTHER PUBLICATIONS

Brunelle et al., A Bipolar Electrode for Vascular Electrocoagulation with Alternating Current, Radiology, Oct. 1980, vol. 137, pp. 239-240.

(56) References Cited

OTHER PUBLICATIONS

Cameron-Miller, An Exceptionally Successful Way to Treat Varicosities, published by Cameron-Miller, Inc., Chicago, Illinois (undated, but available prior to the invention herein).
Chinese Office Action from corresponding Chinese Application No. 200580030082.3, issued Oct. 10, 2008.
Corbett, Phlebology 17:36-40 (2002).
Cragg et al., Endovascular Diathermic Vessel Occlusion, Diagnostic Radiology, 144:303-308, Jul. 1982.
Hejhal et al., "Endovascular Electrocoagulation of Superficial Varices of the Lower Limbs," Surgical outlooks, 1959, vol. XXXVIII-6.
International Search Report for Application No. PCT/US2005/027924 mailed Dec. 19, 2005.
Kianifard et al., "Surgical technique and preliminary results of transluminal occlusion of perforator veins", in "Vascular Surgical Society of Great Britain and Ireland abstracts", British J. of Surgery 2002, vol. 89, pp. 507-526, at 508, 2002 Blackwell Science Ltd.
Office Action Dated Jul. 17, 2009 in corresponding Chinese Patent Application No. 2005800300823. Applicant VNUS Medical Technologies.
Office Action from the Japanese Patent Office (JPO) for Application No. 2007-525036, dated Mar. 30, 2011.
Ogawa et al., Electrothrombosis as a Treatment of Cirsoid Angioma in the Face and Scalp and Varicosis of the Leg, Plastic and Reconstructive Surgery, vol. 3, Sep. 1982, pp. 310-311.
O'Reilly, A Technique of Diathermy Sclerosis of Varicose Veins, The Australian, New Zealand Journal of Surgery, vol. 51, No. 4, Aug. 1981, pp. 379-382.
O'Reilly, Endovenous Diathermy Sclerosis as a Unit of The Armamentarium for the Attack on Varicose Veins; The Medical Journal of Australia, Jun. 1, 1974, p. 900.
O'Reilly, Endovenous Diathermy Sclerosis of Varicose Veins, The Australian, New Zealand Journal of Surgery, vol. 47, No. 3, Jun. 1977, pp. 339-395.
The Whiteley Clinic, "How the Whiteley Clinic has changed Vein Surgery in the UK—1", retrieved from http://www.pioneering-veins-surgery.co.uk/how-the-whiteley-clinic-changed-varicose-vein-surgery-in-the-uk.htm on Nov. 19, 2009.
Watts, Endovenous Diathermy Destruction of Internal Saphenous, British Medical Journal, Oct. 7, 1972, p. 53.
Whiteley et al. (2003) Venous Forum Abstracts, Phlebology 18:1, p. 52.
U.S. Appl. No. 12/626,569, filed Nov. 25, 2009, Brady D. Esch, 2010-0152723, Jun. 17, 2010, Office Action Mar. 1, 2012.
Official Action from Japanese Patent Office (JPO) for Application No. 2007-525036, dated Feb. 2, 2012.
International Search Report for related PCT Application No. PCT/US2010/061951 from International Searching Authority (EPO) mailed Jul. 20, 2011.
Written Opinion for related PCT Application No. PCT/US2010/061951 from International Searching Authority (EPO) mailed Jul. 20, 2011.
U.S. Appl. No. 13/313,562, filed Dec. 7, 2011, Mirizzi et al., 2012/0078246, Mar. 29, 2012, Office Action Jun. 25, 2012 Aug. 27, 2012 Notice of Allowance Sep. 17, 2012.
U.S. Appl. No. 12/860,708, filed Aug. 20, 2010, Nguyen et al., 2011/0166518, Jul. 7, 2011, Office Action Jan. 4, 2013.
U.S. Appl. No. 12/626,569, filed Nov. 25, 2009, Esch et al., 2010/0152723, Jun. 17, 2010, Notice of Allowance Oct. 4, 2012.
U.S. Appl. No. 12/860,708, filed Aug. 20, 2010, Hoa D. Nguyen, 2011-0166518, Jul. 7, 2011, Office Action Jun. 21, 2013.
U.S. Appl. No. 10/914,050, filed Aug. 5, 2004, Mirizzi et al., 2006/0030849, Feb. 9, 2006, Office Actions May 19, 2009 Jul. 3, 2008 May 31, 2007 Notice of Allowance Aug. 23, 2010.
U.S. Appl. No. 11/197,849, filed Aug. 5, 2005, Esch et al., 2006/0189979, Aug. 24, 2006, Office Actions Jan. 14, 2009 May 1, 2008 Notice of Allowance Oct. 7, 2009.
U.S. Appl. No. 12/626,569, filed Nov. 25, 2009, Esch et al., 2010/0152723, Jun. 17, 2010, Office Actions Jun. 8, 2011.
U.S. Appl. No. 12/917,329, filed Nov. 1, 2010, Mirizzi et al., 2011/0144642, Jun. 16, 2011, Office Action May 26, 2011 Notice of Allowance Aug. 25, 2011.

\* cited by examiner

APPARATUS AND METHODS FOR TREATING HOLLOW ANATOMICAL STRUCTURES

CROSS-REFERENCE TO RELATED APPLICATIONS

This application claims priority under 35 U.S.C. §119(e) to U.S. provisional patent application Ser. No. 61/292,112, filed Jan. 4, 2010, titled APPARATUS AND METHODS FOR TREATING HOLLOW ANATOMICAL STRUCTURES; and Ser. No. 61/357,907, filed Jun. 23, 2010, titled APPARATUS AND METHODS FOR TREATING HOLLOW ANATOMICAL STRUCTURES. The entire disclosure of each of the above-mentioned applications is incorporated by reference herein.

BACKGROUND

1. Field

Treatment of hollow anatomical structures such as blood vessels, hollow organs, fallopian tubes, gastric structures, etc.

2. Description of the Related Art

The human venous system of the leg comprises the superficial venous system and the deep venous system, with perforating veins connecting the two systems. The superficial system includes the long or great saphenous vein and the small saphenous vein. The deep venous system includes the anterior and posterior tibial veins, which unite to form the popliteal vein, which in turn becomes the femoral vein when joined by the short saphenous vein. The femoral vein and the great saphenous vein join at the sapheno-femoral junction.

The venous system contains numerous one-way valves for directing antegrade blood flow back to the heart. When an incompetent valve is in the flow path, the valve is unable to close, and retrograde flow of the blood away from the heart cannot be stopped. When a venous valve fails, increased strain and pressure occur within the lower venous sections and overlying tissues, sometimes leading to additional, distal valvular failure. Two venous conditions or symptoms that often result from valve failure are varicose veins and more symptomatic chronic venous insufficiency. Current treatments of venous insufficiency include surgical procedures such as vein stripping, vein-segment transplant, and ligation by ablation.

Vein stripping typically consists of tying off, or ligating, and removing the saphenous vein. Vein segment transplant has been employed in certain organ transplant procedures; however, it is not generally employed in the superficial venous system in humans. Ligation by ablation involves the cauterization or coagulation of vascular lumina using thermal energy applied through a delivery device. Energy introduced into the vein lumen causes the vein wall to shrink in cross-sectional diameter or completely collapse, thereby reducing or completely blocking blood flow through the vein.

An alternative treatment involves placement of an occluding implant in the hollow anatomical structure, such as the great saphenous vein. As an example, the implant can be a fibrous body, optionally textured to impart bulk. The implant causes a partial occlusion of the hollow anatomical structure, followed by a complete or substantially complete occlusion, such as by formation of an organic fibrotic occlusion resulting from the body's natural foreign body healing response.

SUMMARY OF THE INVENTION

A non-exhaustive summary of embodiments disclosed herein follows.

A first embodiment is a method which comprises, in a medical apparatus with a shaft configured for endovascular insertion and having a tissue sensor and an energy application device both located on the shaft: receiving electrical power at a first power level and directing the first-level electrical power to the tissue sensor and not to the energy application device, thereby enabling tissue sensing with the tissue sensor; receiving electrical power at a second power level higher than the first power level; and in response to the second-level electrical power, directing the power to the energy application device, thereby enabling performance of therapy on tissue with the energy application device.

Further optional features and variations of this first embodiment are presented in the following paragraphs. The present disclosure contemplates and includes employing these optional features and variations in the first embodiment (or in any other embodiment summarized or described herein), either alone or in any feasible combination of two or more such optional features and variations.

The first power level can comprise a sub-therapeutic power level.

The first power level can comprise a sub-ablative power level.

The tissue sensor can comprise a pair of electrodes and the first power level can be insufficient to shrink a blood vessel with either the tissue sensor or the energy application device.

The first power level can be less than about 10 milliwatts.

The tissue sensor and the energy application device can be configured for electrical connection to a single power output channel of a power supply. The tissue sensor can comprise a pair of electrodes and the energy application device can comprise an electrically driven heating element which is electrically insulated from any adjacent tissue.

The medical apparatus can comprise a power supply having a first power output channel; the tissue sensor can comprise a pair of electrodes; the energy application device can comprise an electrically driven heating element which is electrically insulated from adjacent tissue; the tissue sensor can be connected to the first power output channel; and the energy application device can be switchably connected to the first power output channel. Directing the second-level electrical power to the energy application device can be performed outside the power supply.

The medical apparatus can comprise a probe assembly which is connectable to a power supply so as to receive electrical power from the power supply; and directing the second-level electrical power to the energy application device can be performed in the probe assembly.

Directing the second-level electrical power to the energy application device can comprise triggering an electronic switch with an increase in power from the first-level electrical power. Receiving electrical power at the first level can comprise receiving the first-level electrical power from a first output channel of a power supply, and receiving electrical power at the second level can comprise receiving the second-level electrical power from the first output channel of the power supply.

The method can further comprise resuming receiving the first-level electrical power, and no longer directing electrical power to the energy application device in response to resumption of receiving the first-level electrical power.

The method can further comprise sensing a type of tissue in contact with the tissue sensor. The method can still further comprise enabling the delivery of electrical power at the second power level only upon sensing a target tissue type with the tissue sensor. The tissue sensor can comprise an electrode pair, and sensing the tissue type can comprise sensing an impedance level via the electrode pair.

A second embodiment is an apparatus. The apparatus comprises a shaft configured for insertion into a blood vessel; a first power lead; a tissue sensor comprising a pair of electrodes located at a distal portion of the shaft; an energy application device comprising an electrically driven heating element which is located at the distal portion of the shaft and electrically insulated from any adjacent tissue. The tissue sensor is electrically connected to the first power lead. The apparatus further comprises an electronic switch that switchably connects the energy application device to the first power lead, the electronic switch being configured to close and electrically connect the energy application device to the first power lead upon receiving electrical power at a level above a relatively low tissue-sensing power level.

Further optional features and variations of this second embodiment are presented in the following paragraphs. The present disclosure contemplates and includes employing these optional features and variations in the second embodiment (or in any other embodiment summarized or described herein), either alone or in any feasible combination of two or more such optional features and variations.

The tissue-sensing power level can be less than about 10 milliwatts.

The electronic switch can comprise a diac-triac.

The electronic switch can comprise a photo-activated switch.

The electronic switch can comprise a solid-state relay.

The electronic switch can be configured to electrically disconnect the energy application device from the first power lead upon receiving electrical power at or below the relatively low tissue-sensing power level.

The apparatus can be configured for connection to a power supply having a first output channel. The tissue sensor is electrically connected to the first output channel upon connection of the apparatus to the power supply, and the energy application device is electrically connected to the first output channel upon connection of the apparatus to the power supply and closure of the electronic switch.

A third embodiment is an apparatus. The apparatus comprises a shaft configured for insertion into a blood vessel; and a tissue sensor comprising a pair of electrodes located at a distal portion of the shaft. The tissue sensor extends to a distal tip of the shaft. The apparatus further comprises an energy application device comprising an electrically driven heating element located at the distal portion of the shaft and proximal of the tissue sensor. The heating element is electrically insulated from any adjacent tissue. The tissue sensor extends proximally from the distal tip of the shaft by a distance of less than about 10 mm, and the electrodes of the tissue sensor are separated by an electrode gap of 0.3 mm to 1.0 mm.

Further optional features and variations of this third embodiment are presented in the following paragraphs. The present disclosure contemplates and includes employing these optional features and variations in the third embodiment (or in any other embodiment summarized or described herein), either alone or in any feasible combination of two or more such optional features and variations.

The electrodes can include a distal electrode and a proximal electrode, and the proximal electrode can extend along the shaft by a distance of 0.5 mm to 2.0 mm.

The electrodes can include a distal electrode and a proximal electrode, and the proximal electrode can extend along the shaft by a distance of 0.6 to 1.0 mm.

The tissue sensor can extend proximally from the distal tip of the shaft by a distance of less than about 4 mm.

The apparatus can further comprise a first power lead; the tissue sensor can be electrically connected to the first power lead; and the energy application device can switchably connected to the first power lead via a switch that closes upon receipt of electrical power at a level that exceeds a tissue sensing power level.

A fourth embodiment comprises a method. The method comprises inserting a shaft into tissue of a patient, the shaft having both a tissue sensor and a separate therapeutic energy application device located at a distal portion of the shaft; and moving the shaft through the tissue toward a target blood vessel. The method further comprises, while inserting or moving the shaft, delivering electrical power to the tissue sensor and thereby sensing the type of tissue in which the distal portion of the shaft is located; positioning the distal portion of the shaft at least partially in the target blood vessel; sensing the position of the distal portion of the shaft in the target blood vessel via the tissue sensor; after sensing the position of the distal portion of the shaft in the target blood vessel, increasing the level of power delivered to the shaft and thereby causing the power to be directed to the therapeutic energy application device; and heating the target blood vessel with the therapeutic energy application device.

Further optional features and variations of this fourth embodiment are presented in the following paragraphs. The present disclosure contemplates and includes employing these optional features and variations in the fourth embodiment (or in any other embodiment summarized or described herein), either alone or in any feasible combination of two or more such optional features and variations.

The method can further comprise shrinking the target blood vessel by heating it with the therapeutic energy application device.

Delivering electrical power to the tissue sensor can further comprise not delivering electrical power to the therapeutic energy application device.

The tissue sensor can comprise first and second electrodes, and the therapeutic energy application device can comprise an electrically driven heating element which is electrically insulated from adjacent tissue. Increasing the level of power can further comprise triggering an electronic switch that directs power to the therapeutic energy application device. Inserting the shaft can comprise puncturing a skin surface with a sharp tip of the shaft.

Increasing the power level can comprise increasing the power to a level which is sufficient to shrink the target blood vessel with the therapeutic energy application device.

A fifth embodiment comprises a method of performing therapy on tissue using a medical apparatus. The apparatus includes a shaft configured for insertion into a hollow anatomical structure (HAS) and has a tissue sensor and a therapeutic energy application device both located on the shaft. The method comprises receiving electrical power at a first power level and directing the first-level power to the tissue sensor and not to the therapeutic energy application device, thereby enabling tissue sensing with the tissue sensor; receiving electrical power at a second power level higher than the first-level power; and, in response to receipt of the second-level power, directing the second-level power to the therapeutic energy application device, thereby enabling performance of therapy on the tissue with the therapeutic energy application device.

Further optional features and variations of this fifth embodiment are presented in the following paragraphs. The present disclosure contemplates and includes employing these optional features and variations in the fifth embodiment (or in any other embodiment summarized or described herein), either alone or in any feasible combination of two or more such optional features and variations.

Directing the second-level power to the energy application device can comprise closing a switch with an increase in power from the first-level power, where the power increase triggers the switch closing. The switch can optionally be located outside a power supply that generates the electrical power.

The method can further comprise resuming receiving the first-level power and directing the first-level power to the tissue sensor and not to the energy application device. Resuming receiving the first-level power can optionally comprise opening the switch with a decrease in power from the second-level power, where the power decrease triggers the switch opening.

The first-level power can be received from a first output channel of a power supply. The second-level power can optionally be received from the first output channel of the power supply.

The method can further comprise sensing a type of tissue in contact with the tissue sensor. The method can further optionally comprise enabling delivery of the second-level power only upon sensing a target tissue type with the tissue sensor.

The first-level power can be a sub-therapeutic power level.

The first-level power can be a sub-ablative power level.

The first-level power can be insufficient to shrink the HAS.

The first-level power can be less than about 10 mW, or less than 10 mW.

The tissue sensor can comprise a pair of electrodes. Sensing a type of tissue in contact with the tissue sensor can optionally comprise sensing an impedance level via the electrode pair.

The energy application device can comprise an electrically driven heating element that is electrically insulated from any adjacent tissue. Directing the first-level power to the tissue sensor and not to the therapeutic energy application device can optionally comprise improving the accuracy of the tissue sensor.

The HAS can be a vascular structure.

A sixth embodiment comprises an apparatus for performing therapy on tissue. The apparatus comprises an elongate shaft having a distal portion configured for insertion into a hollow anatomical structure (HAS); a power lead; a tissue sensor located at the shaft distal portion and configured to receive power through the power lead at a relatively low tissue-sensing level; a therapeutic energy application device located at the shaft distal portion and configured to selectively receive power through the power lead at a relatively high tissue-treatment level; and a switch including an open position and a closed position. The tissue sensor is electrically connected to the power lead, and the therapeutic energy application device is electrically connected to the power lead only when the switch is in the closed position.

Further optional features and variations of this sixth embodiment are presented in the following paragraphs. The present disclosure contemplates and includes employing these optional features and variations in the sixth embodiment (or in any other embodiment summarized or described herein), either alone or in any feasible combination of two or more such optional features and variations.

The switch can be in the open position when power is received through the power lead at the tissue-sensing level, and the switch can automatically close to electrically connect the energy application device to the power lead when power is received through the power lead at a level above the tissue-sensing level. The tissue-sensing power level can optionally be less than about 10 mW, or less than 10 mW. The switch can optionally be a diode for alternating current (DIAC), a triode for alternating current (TRIAC), photo-activated, and/or a solid-state relay.

The tissue sensor can comprise a pair of electrodes.

The energy application device can comprise an electrically driven heating element that is electrically insulated from any adjacent tissue.

The power lead can be configured to be connected to a first output channel of a power supply. The tissue sensor can optionally be electrically connected to the power supply upon connection of the power lead to the first output channel. The energy application device can optionally be electrically connected to the power supply upon connection of the power lead to the first output channel and closure of the switch.

A seventh embodiment comprises an apparatus for performing therapy on tissue. The apparatus comprises an elongate shaft having a distal portion configured for insertion into a hollow anatomical structure (HAS); a tissue sensor including a pair of electrodes located at the shaft distal portion and extending to a distal tip of the shaft; and a therapeutic energy application device located at the shaft distal portion proximal of the tissue sensor. The tissue sensor extends proximally from the shaft distal tip by a distance of less than about 10 mm, and the electrodes of the tissue sensor are separated by an electrode gap of about 0.3 mm to about 1.0 mm.

Further optional features and variations of this seventh embodiment are presented in the following paragraphs. The present disclosure contemplates and includes employing these optional features and variations in the seventh embodiment (or in any other embodiment summarized or described herein), either alone or in any feasible combination of two or more such optional features and variations.

The energy application device can comprise an electrically driven heating element that is electrically insulated from any adjacent tissue.

The electrodes of the tissue sensor can be separated by an electrode gap of about 0.4 mm.

The electrodes can include a distal electrode and a proximal electrode, and the proximal electrode can extend along the shaft by a distance of about 0.5 mm to about 2.0 mm. The proximal electrode can optionally extend along the shaft by a distance of about 0.6 mm to about 1.0 mm.

The tissue sensor can extend proximally from the shaft distal tip by a distance of less than about 4 mm.

The apparatus can further comprise a power lead and a switch, wherein the tissue sensor is electrically connected to the power lead, and the energy application device is electrically connected to the power lead only when the switch is in a closed position. The switch can optionally automatically close in response to receipt of electrical power at a level that exceeds a relatively low tissue-sensing level.

An eighth embodiment comprises a method of performing therapy on tissue using a medical apparatus. The apparatus includes a shaft configured for insertion into a hollow anatomical structure (HAS) and has a tissue sensor and a therapeutic energy application device both located at a distal portion of the shaft. The method comprises inserting the shaft into tissue; moving the shaft through the tissue toward the HAS; while inserting or moving the shaft, delivering electrical power to the apparatus, directing the power to the tissue sensor, and sensing a type of tissue in which the distal portion of the shaft is located; positioning the shaft distal portion at least partially within the HAS; sensing, via the tissue sensor, that the shaft distal portion is positioned at least partially within the HAS; after sensing that the shaft distal portion is positioned at least partially within the HAS, increasing a level of the power delivered to the apparatus, the increased power level causing the power to be automatically directed to the therapeutic energy application device; and heating the HAS with the therapeutic energy application device.

Further optional features and variations of this eighth embodiment are presented in the following paragraphs. The present disclosure contemplates and includes employing these optional features and variations in the eighth embodiment (or in any other embodiment summarized or described herein), either alone or in any feasible combination of two or more such optional features and variations.

The HAS can comprise a vascular structure, and heating the vascular structure can cause it to shrink.

The method can further comprise not delivering electrical power to the energy application device while moving the shaft through the tissue toward the HAS. Not delivering electrical power to the energy application device can optionally comprise improving the performance of the tissue sensor.

The tissue sensor can comprise a pair of electrodes. Sensing the type of tissue in which the distal portion of the shaft is located can optionally comprise sensing an impedance level via the electrode pair.

The energy application device can comprise an electrically driven heating element that is electrically insulated from any adjacent tissue.

Directing the power to the energy application device can comprise automatically closing a switch in response to the increased power level. The switch can optionally be located outside a power supply that generates the electrical power.

Increasing the power level can comprise increasing the power to a level sufficient to shrink the HAS with the energy application device.

Inserting the shaft can comprise puncturing a skin surface with a sharp tip of the apparatus.

Certain objects and advantages of the disclosed embodiments are described herein. Of course, it is to be understood that not necessarily all such objects or advantages may be achieved in accordance with any particular embodiment. Thus, for example, an embodiment may be practiced or carried out in a manner that achieves or optimizes one advantage or group of advantages as taught herein without necessarily achieving other objects or advantages as may be taught or suggested herein.

Despite the foregoing discussion of certain embodiments, only the appended claims, and such other claims as may be presented in the future based on the disclosure herein (and not the present Summary), are intended to define the invention(s) protected hereby. The summarized embodiments, and other embodiments, are presented in the following detailed description having reference to the attached figures.

DETAILED DESCRIPTION OF THE PREFERRED EMBODIMENT

Figure 1:
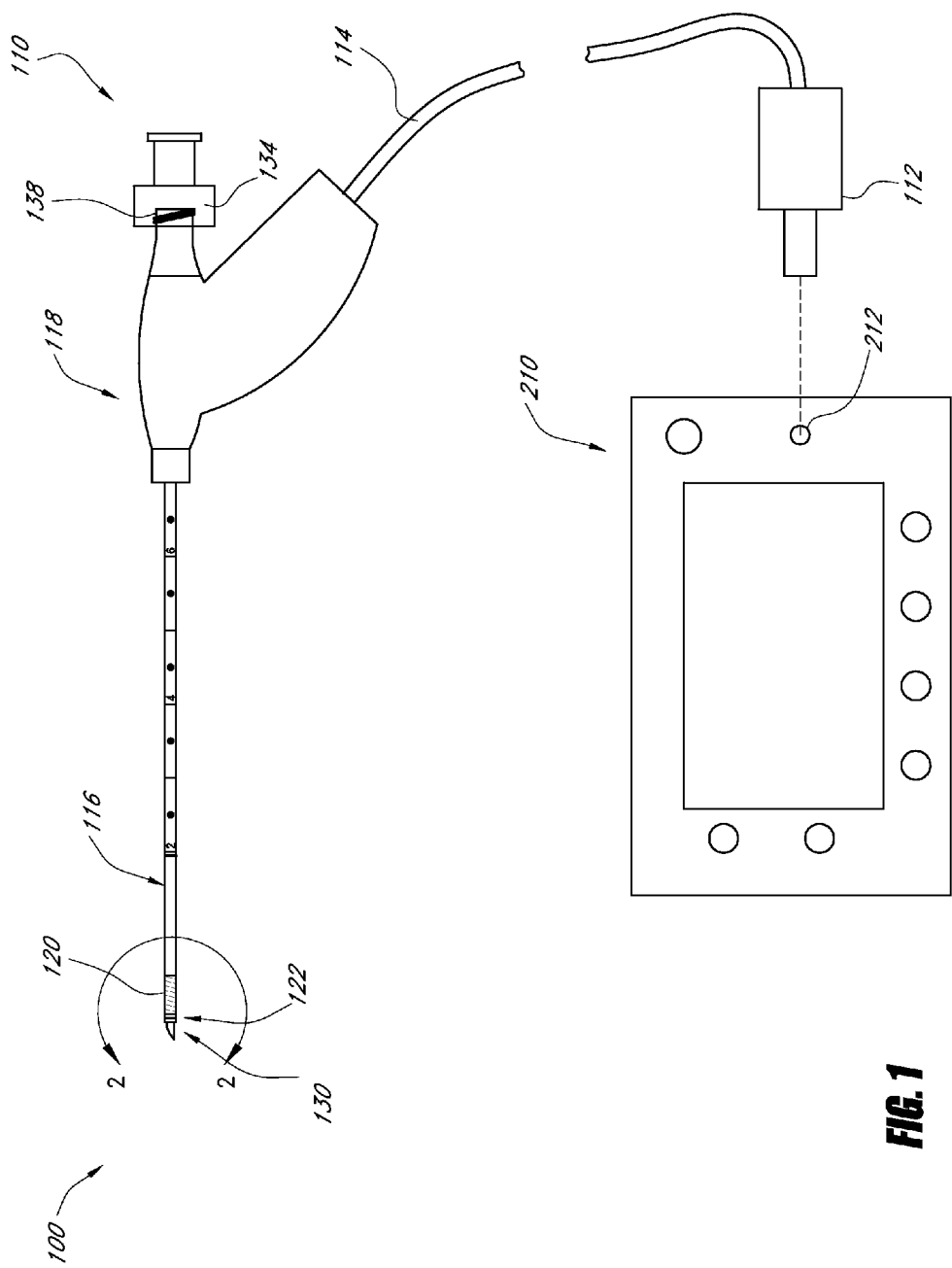
FIG. 1 is a side elevation view of one embodiment of a probe for treating a hollow anatomical structure, along with an associated power supply.

FIG. 1 depicts a treatment system 100 that can be used to treat hollow anatomical structures ("HAS's") such a blood vessels, for example arteries or veins, including veins of the leg such as perforator veins. The treatment system 100 generally comprises a probe 110 configured for insertion into the lumen of the HAS under treatment, and a power supply 210 such as an AC or DC electrical generator, or a radiofrequency ("RF") generator. The power supply is configured for electrical communication with the probe 110 via a socket 212 which can receive and mate with a connector 112 which in turn communicates with the probe 110 via a cord 114.

Figure 2:
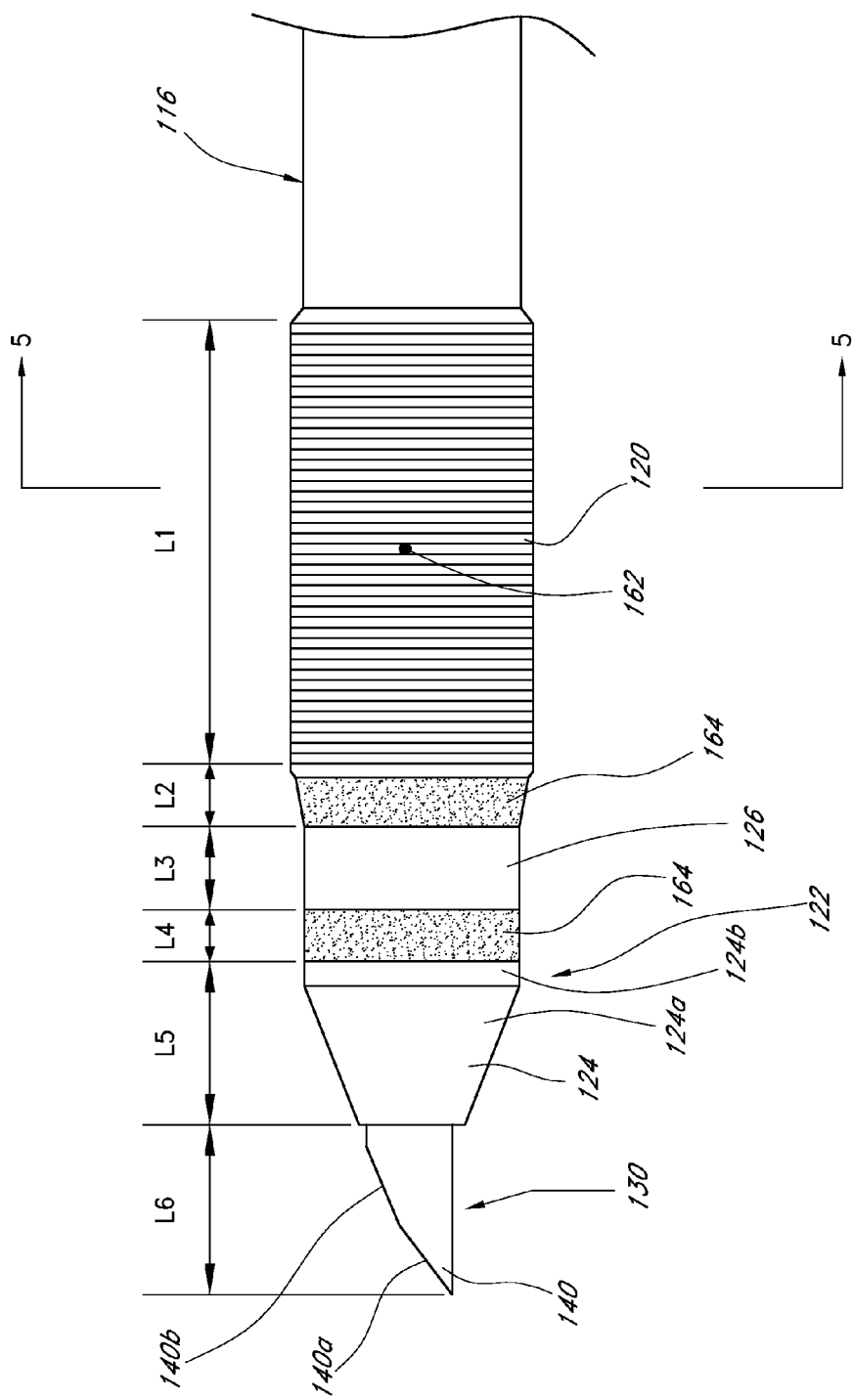
FIG. 2 is a detail view of a distal tip portion of the probe of FIG. 1.

As best seen in FIGS. 1 and 2, the probe 110 generally comprises an elongate shaft assembly 116 and a handle 118 located at the proximal end of the shaft 116. At or near the distal end of the shaft 116 is an energy delivery device in the form of a heating coil 120, and a tissue sensor in the form of an electrode pair 122 (e.g., comprising distal and proximal electrodes 124, 126). The shaft 116 can be 50-150 mm, or 80-120 mm, or about 80 mm in length, or any other suitable length, measured from the distal end of the handle 118 to the distal end of the distal electrode 124.

The depicted electrodes 124, 126 are arranged as a longitudinally-spaced pair, with one electrode 126 on the proximal side and the other electrode 124 on the distal side of a gap located between the two. Each such electrode is preferably in the form of a ring that extends completely around the circumference of the shaft 116. Alternatively, the electrodes 124, 126 can be arranged as one or more radially-spaced pairs, with each electrode extending only partially around the circumference of the shaft 116, and one or more gaps located radially between the electrodes. Such electrodes are preferably longitudinally aligned at their respective distal and proximal edges, and preferably have equal lengths along the longitudinal direction of the shaft 116.

The depicted electrodes 124, 126 are located distal of the coil 120. Alternatively, the electrodes can be located proximal of the coil, or midway along the coil, or in a combination of such locations (e.g., one pair or electrode located proximal of the coil and a second pair or electrode located distal of the coil).

An energy delivery device other than the coil 120 can be employed, such as a heating element other than a coil (e.g. a resistive sleeve or tube, or a wire or wires in a form other than a coil), electrode(s), a microwave antenna, a light-energy emitter such as an LED, or a laser/light-energy reflector, refractor or scattering device. The emitter, reflector, refractor or scatterer can be employed to emit or direct laser/light in a sideways (or partially sideways) direction relative to the longitudinal axis of the shaft 116. The shaft 116 may also include or be configured to receive a fiber optic (not shown) that can be employed to supply laser/light energy from an energy source to the reflector, refractor, or scattering device, or the fiber optic can be employed alone to direct light energy such as laser light in a distal (or partially distal) direction away from the distal end of the shaft 116. In addition, any suitable tissue sensor other than the depicted electrode pair 122 can be employed.

Figure 3:
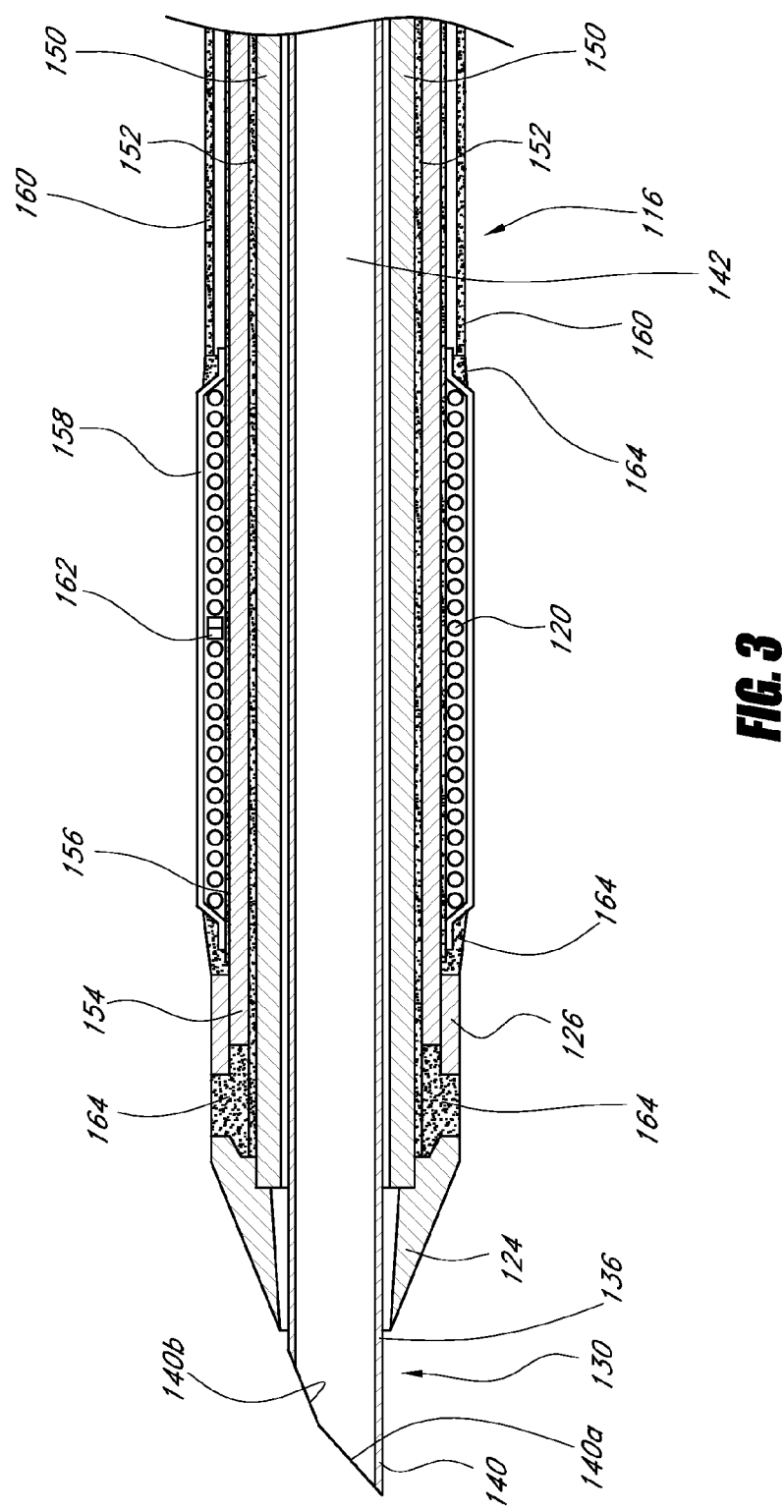
FIG. 3 is a sectional view of the detail view of FIG. 2.
Figure 4:
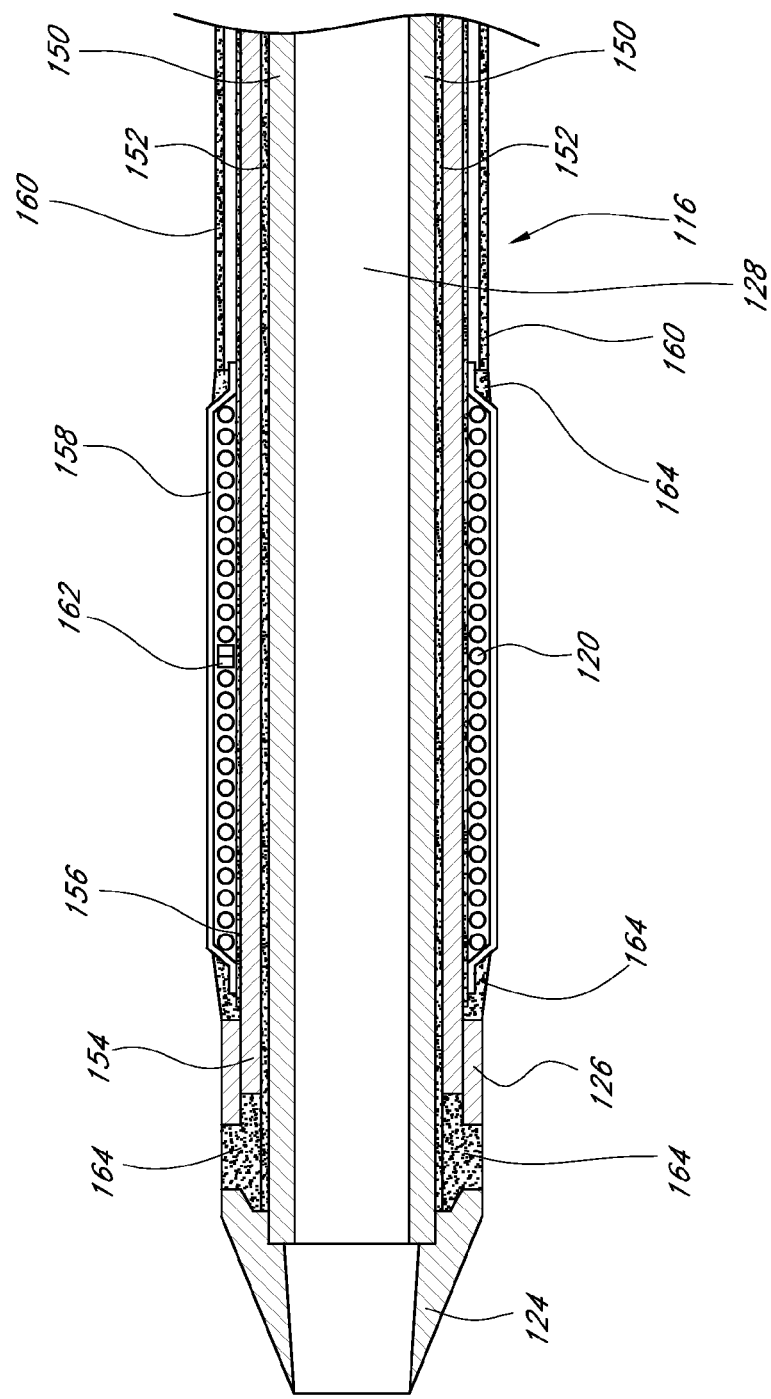
FIG. 4 is a sectional view of the detail view of FIG. 2, with a needle removed.

Referring to FIGS. 1-4, the probe 110 can receive a removable needle 130 that extends through a lumen 128 of the shaft 116, and through the handle 118 to join a needle coupler 134, to which the needle shaft 136 is fixed. The needle coupler can comprise a female luer fitting that can removably engage a male luer fitting 138 located at the proximal end of the handle 118. To remove the needle 130 from the probe 110, the user unscrews the needle coupler 134 from the fitting 138 of the handle 118 and withdraws the needle shaft 136 proximally from and out of the probe shaft lumen 128. (FIG. 4 shows a distal portion of the probe 110 with the needle 130 removed.) The reverse can be performed to insert and couple the needle to the probe 110.

As best seen in FIGS. 2 and 3, the needle 130 includes a sharpened distal tip 140 configured for puncturing and penetrating tissue. In the depicted embodiment, the distal tip 140 can incorporate a compound bevel, with a distal bevel 140*a* and a proximal bevel 140*b*.

The needle 130 preferably includes a central lumen 142 that extends through the entire length of the needle shaft 136 and communicates with a passage (not shown) formed in the proximal portion of the needle coupler 134. The needle lumen 142 and passage are preferably dimensioned to receive and permit a guidewire (not shown) to pass therethrough. This configuration of the needle lumen 142 and coupler 134 enables a user to pass a guidewire, if desired, from the distal end of the needle 130, through the needle lumen 142 and the coupler 134, to an area proximal of the coupler 134. When the needle 130 is coupled to the probe 110, a guidewire so inserted will also extend through the probe shaft 116 and handle 118, to an area proximal of the probe-needle assembly.

One embodiment of an internal configuration of the probe shaft 116 can be seen in FIGS. 3 and 4, although any other suitable configuration may be employed. The shaft 116 comprises a hypotube 150 which is preferably rigid (so as to impart rigidity to the probe shaft 116 as a whole, where such a hypotube is employed) and formed from an electrically conductive material such as stainless steel (e.g., type 304 stainless steel). The hypotube 150 can extend the length of the shaft 116 to the distal electrode 124, to which the hypotube 150 is firmly coupled and electrically connected. Welding (e.g. laser welding) can be used to connect the distal electrode 124 and the hypotube 150, although other techniques such as adhesives or threaded engagement can be employed. A layer of electrical insulation 152 covers the outer surface of the hypotube 150 proximal of the distal electrode 124. A proximal electrode conductor 154 is located adjacent and radially outward of the insulation 152. The conductor 154 can extend the length of the shaft 116 to the proximal electrode 126, to which the conductor 154 is firmly coupled and electrically connected. The conductor is formed from an electrically conductive material such as stainless steel (e.g., type 304 stainless steel), and can take the shape of a tube, or of a strip or bar forming a wall portion of a tube, the balance of which tube is a non-conductive material. The conductor 154 is connected to the proximal electrode 126 via welding (e.g. laser welding), threads, adhesives or the like.

Another layer of electrical insulation 156 (e.g. polyimide of about 0.002 inch thickness) covers the outer surface of the proximal electrode conductor 154, and the coil 120 is adjacent to and wound around the insulation 156. An outer electrically insulating cover 158 (comprising, for example, polyethylene terephthalate (PET) of about 0.002 inch thickness) can be shrink-wrapped or otherwise adhered around the coil 120. An electrically insulating outer shaft housing 160 can extend the length of the shaft 116 to a location close to and/or abutting the proximal end of the coil 120 and insulating cover 158. The outer shaft housing 160 can comprise polyimide tubing and have an outside diameter of 1.8 mm to 2.2 mm, or about 2 mm.

In one embodiment, the coil 120 can comprise an insulated wire (comprising, for example, annealed Alloy 52 wire of about 0.005 inch diameter and specific resistance of about 260 ohms circular mil per foot, with polyimide insulation of about 0.0005 inch thickness) that is bent in half to provide a bifilar configuration. The bifilar wire is wound around the shaft from the distal end to the proximal end, with the bend of the wire at the distal end of the coil. With the coil thus configured, both conductive ends or terminals of the coil wire are located at the proximal end of the coil. A pair of leads (not shown in FIG. 3 or 4) are connected to the coil to provide electrical power thereto. The coil leads can be routed along the shaft from the proximal end of the coil 120, proximally through the space between the insulation layer 156 and the outer shaft housing 160 (and/or between the insulation layer 152 and the outer shaft housing 160), and into the handle 118. The coil 120 can have a length L1 from about 4.5 mm to about 5.5 mm, or about 5.0 mm, or any other suitable length; and have an outside diameter of 2 mm to 2.5 mm, or about 2.2 mm, or any other suitable diameter.

A temperature sensor 162 (e.g., a thermocouple (such as a K-type bifilar thermocouple), thermistor, or the like) is preferably positioned within or adjacent to the coil 120. In the depicted embodiment, the temperature sensor 162 is located about midway along the length of the coil, in a gap formed between adjacent winds of the coil. A pair of leads (not shown in FIG. 3 or 4) are connected to the temperature sensor 162 to provide temperature information to the power supply 210. The sensor leads can pass from the temperature sensor 162, through an opening in the insulation 156, and proximally along the shaft between the insulation layers 152, 156 (and/or between the insulation layer 152 and the outer shaft housing 160), and into the handle 118.

An electrically non-conductive adhesive 164 can be used to fill in the gap between the electrodes 124, 126; any gap between the proximal electrode 126 and the coil 120/cover 158; and any gap between the coil 120/cover 158 and the outer shaft housing 160.

The probe shaft 116 depicted in FIGS. 1-4 is constructed to be rigid and have sufficient column strength to facilitate tissue puncturing and/or penetration, e.g. as described in connection with FIGS. 11-15 below. Alternatively, the probe shaft can be flexible like a catheter configured for navigating tortuous vasculature.

The proximal electrode 126 preferably comprises a cylindrical "ring" with a substantially flat outer surface as viewed from the side in FIGS. 2-4. The exposed outer surface of the proximal electrode 126 preferably surrounds the entire shaft 116, and extends along the shaft by a length L3 of 0.5 mm to 2.0 mm, or 0.6 to 1.0 mm, or about 0.69 mm. The proximal electrode 126 can be about 0.25 mm thick, and spaced distally from the distal end of the coil 120 by a length L2 of 0.5 to 4 mm, or about 0.7 mm. Other configurations for the proximal electrode 126 can be employed, such as a bulged and/or tapering outer surface.

The gap length L4 between the distal and proximal electrodes 124, 126 is from 0.1 mm to 2 mm, or 0.3 mm to 1.0 mm, or from 0.3 mm to 0.5 mm, or from 0.35 mm to 0.45 mm, or about 0.4 mm.

The distal electrode 124 can form a distal conical portion 124a and a relatively short proximal cylindrical portion 124b. The distal electrode 124 preferably has an overall length L5 of 0.5 mm to 5 mm, or 1.1 mm to 1.4 mm, or about 1.2 mm, with the proximal cylindrical portion 124b taking up 0.1 mm to 0.3 mm of that length. The taper angle of the distal conical portion 124a can be from 18 to 22 degrees with respect to the horizontal (i.e. a line parallel to the longitudinal axis of the probe shaft 116). The taper angle of the distal conical portion 124a can be the same as that of the proximal bevel 140b of the needle 130.

The electrodes 124, 126 preferably have the same outside diameter from 1.5 to 2.2 mm, or about 1.74 mm. The distal electrode 124 can have an inside diameter at its distal tip of 0.5 mm to 1.2 mm, or about 0.97 mm.

The needle 130 can extend beyond the distal end of the distal electrode 124 by a distance L6 of 2 to 10 mm, or about 2.5 mm. The proximal bevel 140b of the needle 130 can preferably be from 18 to 22 degrees with respect to the horizontal, and the distal bevel 140a can preferably be from 28 to 32 degrees with respect to the horizontal. The distal bevel 140a can optionally comprise a compound bevel cut in two separate planes tilted with respect to each other about the central longitudinal axis of the probe shaft by an included angle of about 64 degrees between the cut planes.

The needle 130 can have an outside diameter of 0.4 mm to 1.1 mm, or about 0.87 mm; and an inside diameter of 0.3 mm to 0.9 mm, or about 0.63 mm. The needle 130 and the electrodes 124, 126 can be formed from a metal such as stainless steel, e.g. type 304 stainless steel.

Figure 5:
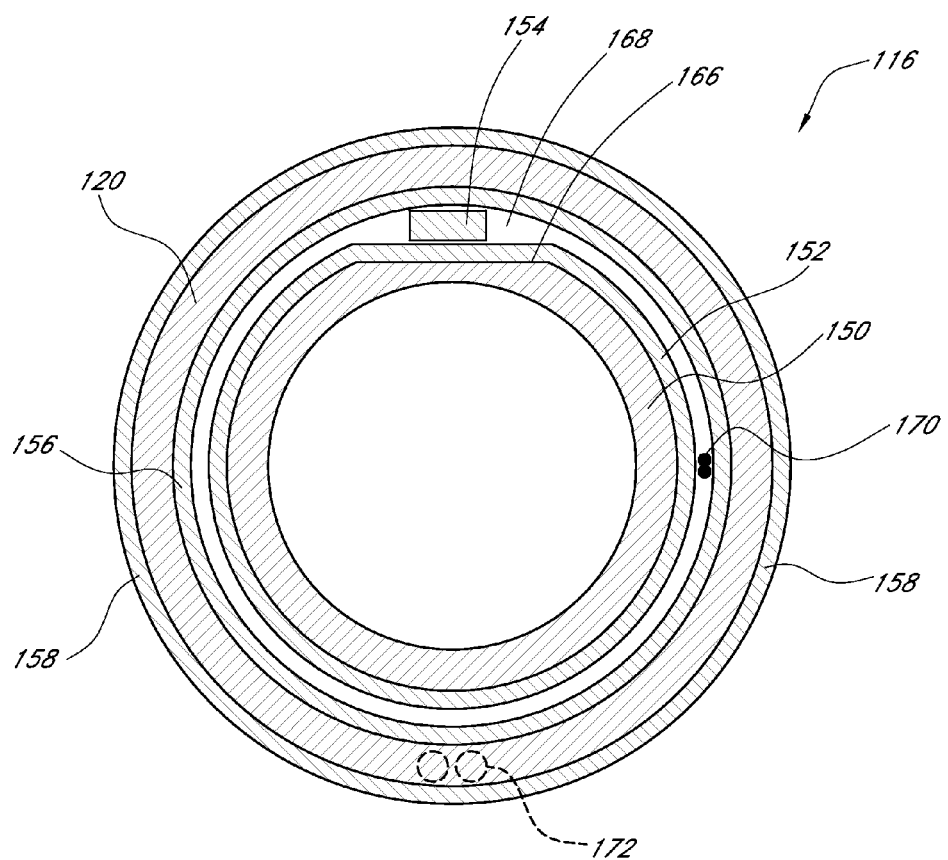
FIG. 5 is an axial sectional view of the detail view of FIG. 2, taken along the line 5-5 shown in FIG. 2.

FIG. 5 is a cross-sectional view of one possible configuration for the probe shaft 116. In this configuration, the hypotube 150 has a flattened, low-profile wall portion 166 formed on one side of the hypotube. The low-profile wall portion 166 can be cut or machined from the sidewall of the hypotube to create a flat outer surface of the hypotube which overlies a thinner section of the hypotube sidewall. Accordingly, the radial extent of the hypotube 150 is smaller in the area of the low-profile wall portion 166, which provides radial dimensional relief in the construction of the shaft 116. The low-profile wall portion 166 can optionally be present only along a distal portion of the hypotube, e.g. along the distal-most 15-25 mm thereof. The low-profile wall portion 166 can further optionally terminate just before the distal end of the hypotube 150, to provide a "full ring" contact surface abutting the distal electrode 124.

The insulation layer 152 is adhered to the outer surface of the hypotube 150, and conforms to the flat outer surface of the low-profile wall portion 166. The insulation layer 156 is generally cylindrical and provides an enlarged gap 168 where it overlies the low-profile wall portion 166. The gap 168 accommodates the proximal electrode conductor 154, which can be made relatively large to enhance conductivity and electrode performance.

The temperature sensor leads 170 can also be located in the gap between the insulation layers 152, 156, and can be positioned about 90 degrees away from the proximal electrode conductor 154 to avoid electrical contact or interference between the two. The coil leads 172 can extend proximally from the proximal end of the coil 120, beneath the outer shaft housing 160 (not shown in FIG. 5).

Optionally, to accommodate use of single output channel of a power supply for both tissue sensing and therapeutic power delivery, the coil 120 and electrodes 124, 126 can be connected in parallel to a single pair of electrical contacts (which connect to two corresponding contacts of the power output channel upon connection of the probe to the power supply).

Figure 6:
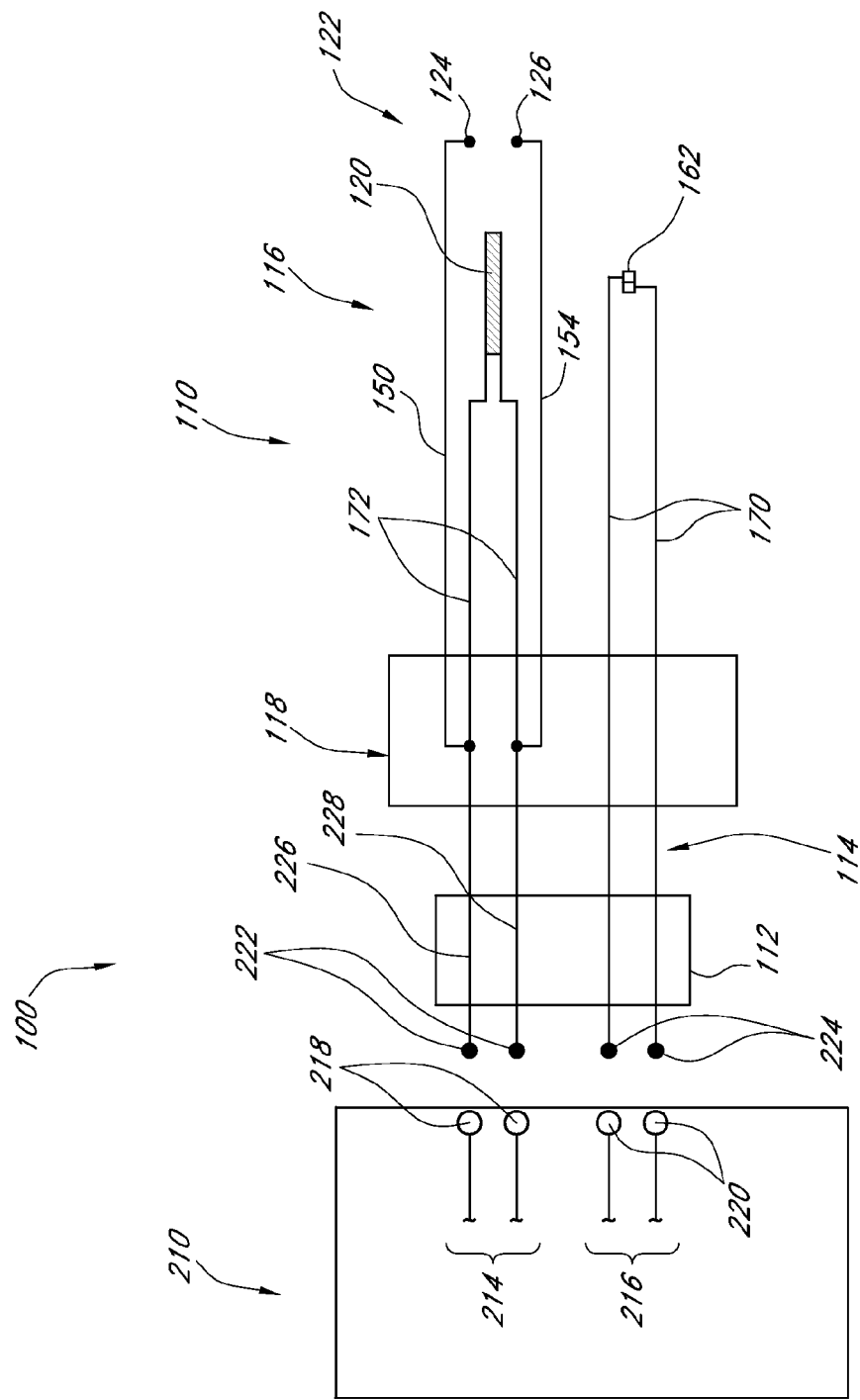
FIG. 6 is a schematic view of circuitry contained in the probe and power supply of FIG. 1.

FIG. 6 provides a schematic view of one possible such arrangement. The depicted power supply 210 has a first output channel 214 that can be used for both tissue sensing and delivery of therapeutic power, and a second output channel 216 that can be used for temperature sensing. The first and second channels 214, 216 terminate in pairs of contacts 218, 220 respectively, which in turn electrically connect to contact pairs 222, 224 upon connection of the probe connector 112 to the power supply 210 (e.g. via the socket 212 best seen in FIG. 1). The temperature sensor leads 170 extend from the contacts 224, through the connector 112 and the handle 118, along the probe shaft 116 to the temperature sensor 162. Thus the power supply 210 can electrically communicate with and receive temperature information via the sensor 162.

First and second dual-purpose conductors 226, 228 extend from the contacts 222, through the plug 112, and into the handle 118. There the conductor 226 splits into a distal electrode conductor 150 (at least a portion of which can comprise the hypotube 150; see FIG. 3) and one of the coil leads 172, and the conductor 228 splits into the proximal electrode conductor 154 and the other of the coil leads 172.

The arrangement of FIG. 6 offers the advantage of employing a single output channel 214 for both tissue sensing and tissue therapy. For example, the power supply 210, through the channel 214, can pass a low power level (e.g. less than about 10 milliwatts RMS, or less than about 100 milliwatts peak; or less than about 10 milliwatts DC; or about 2.3 milliwatts RMS) suitable for sensing with the electrodes 124, 126, and subsequently or otherwise separately pass a high power level (e.g. greater than about 10 milliwatts RMS, or greater than about 100 milliwatts peak; or greater than about 10 milliwatts DC) suitable for heating the coil 120 sufficiently to perform therapy on tissue (e.g. to shrink a blood vessel such as a vein).

However, the inventors found that the probe of FIG. 6 yielded unsatisfactory tissue sensing performance via the electrodes 124, 126. When the probe of FIG. 6 was used to sense impedance across the electrodes 124, 126 (and thereby determine the medium such as air, blood, tissue, saline, etc. in which the probe tip was positioned), insufficient separation was observed between impedances sensed with the electrodes in contact with the various relevant media. Notwithstanding the foregoing, the probe of FIG. 6 functions properly for performing tissue treatments such as shrinking blood vessels, and the present disclosure includes the use of the probe of FIG. 6 in combination with other features, methods, and apparatus disclosed herein.

Figure 7:
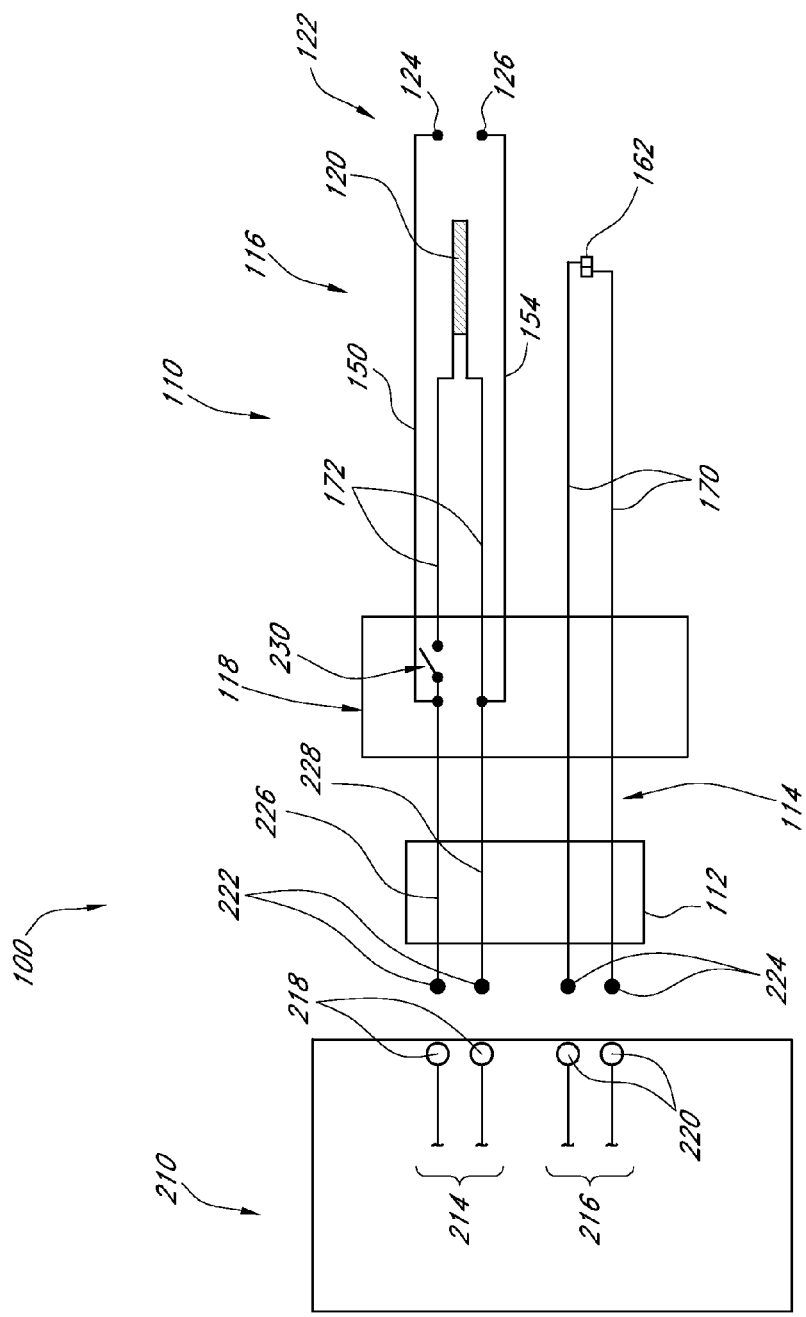
FIG. 7 is a schematic view of circuitry contained in the probe and power supply of FIG. 1.

As seen in FIG. 7, the inventors further found that adding a switch 230 to the probe 110 yielded much better tissue sensing performance. Such improved performance was observed when the switch 230 was used to disconnect the coil 120 from the circuit between the contacts 222 while sensing impedance across the electrodes 124, 126. With the coil 120 thus disconnected, significantly higher separation was observed between impedances sensed with the electrodes in contact with the various relevant media (e.g., air, blood, tissue, saline, etc.). The higher separation in turn facilitates accurately determining which medium or tissue type the electrodes are in contact with, or the body location in which the probe tip is positioned, based on the measured impedance.

To enable use of the coil 120 to perform therapeutic heating of tissue, the switch 230 is closed, thereby connecting the coil 120 to the circuit between the contacts 222, and a therapeutic level of power is delivered through the circuit (via the channel 214) and the coil 120.

The switch 230 can be implemented in different forms in various embodiments. For example, the switch 230 could be a manually operable switch positioned on the handle 118 or other part of the probe 110, or on the power supply 210. Or an automatically triggered switch could be employed, e.g. an automatically triggered electronic switch that responds to an increase in current, power, voltage, etc. delivered to the probe 110 when delivery of a therapeutic level of power is initiated. Such an automatically triggered electronic switch could comprise a diac-triac, or a solid state relay (SSR), for example a photo-coupled SSR such as a photo-activated mosfet switch. In some embodiments disclosed herein, the switch is positioned in the probe 110; alternatively, the switch can be positioned in and form part of the power supply 210.

In testing, the inventors found that the diac-triac performed the switching function properly but attained an undesirably high operating temperature at the radio frequencies (e.g. 460 kHz) commonly output by electrosurgical power supplies (in contrast to the lower 60 Hz frequency in the typical household applications for the diac-triac). Nonetheless the probe 110 will function with the diac-triac and such is considered within the scope of the present disclosure.

Figure 8:
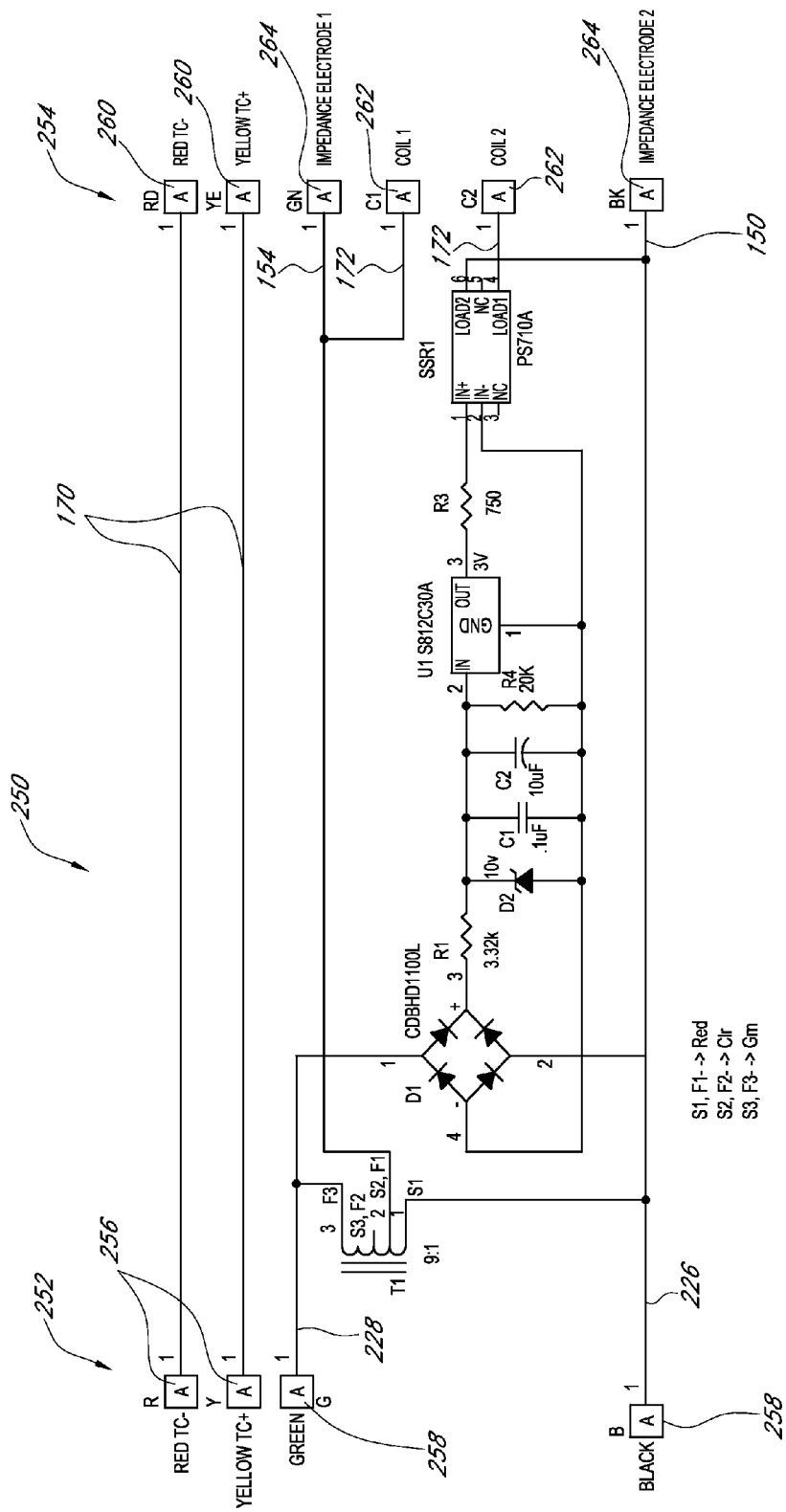
FIG. 8 is a schematic view of circuitry implementing a switch in the circuitry of FIGS. 6 and 7.

FIG. 8 schematically depicts one possible implementation of an SSR electronic autoswitch in a circuit 250 that can optionally take the form of one or more circuit boards located in the handle 118 and/or the plug 112. The depicted circuit 250 includes a number of plug-side contacts 252 (e.g., connection pads) and shaft-side contacts 254 (again, e.g., connection pads). The plug-side contacts 252 include a pair of temperature sensor contacts 256 which couple to and thereby continue the temperature sensor leads 170 into the circuit 250; thus, the temperature sensor contacts 256 communicate with the contacts 224 of the plug 112 (and, ultimately, the channel 216 of the power supply 210 upon connection of the plug to the power supply). The plug-side contacts 252 also include a pair of dual-purpose contacts 258 which couple to and thereby continue the dual-purpose conductors 226, 228 into the circuit 250; thus, the contacts 258 communicate with the contacts 222 of the plug 112 (and, ultimately, the channel 214 of the power supply 210 upon connection of the plug to the power supply).

The shaft-side contacts 254 include a pair of temperature sensor contacts 260 which couple to and thereby continue the temperature sensor leads 170 from the circuit 250 towards and/or into the probe shaft 116. Thus the temperature sensor contacts 260 communicate with the temperature sensor 162.

The shaft-side contacts 254 also include a pair of coil contacts 262 which couple to and thereby continue the coil leads 172 from the circuit 250 towards and/or into the probe shaft 116. Thus the coil contacts 262 communicate with the coil 120. The shaft-side contacts 254 also include a pair of electrode contacts 264 which couple to and thereby continue the electrode conductors 150, 154 from the circuit 250 towards and/or into the probe shaft 116. Thus the electrode contacts 264 communicate with the electrodes 124, 126.

With further reference to FIG. 8, the circuit 250, while the solid state relay SSR1 is open, can be employed to pass a (relatively low) tissue sensing power (e.g. less than about 10 milliwatts RMS, or less than about 100 milliwatts peak; or less than about 10 milliwatts DC; or about 2.3 milliwatts RMS) from the power supply channel 214 through the electrodes 124, 126 in an initial "Measure Mode" during which impedance can be measured across the electrodes to, e.g., determine the medium or body location in which the probe tip is positioned. Upon delivery of a relatively high, therapeutic level of power (e.g. greater than about 10 milliwatts RMS, or greater than about 100 milliwatts peak; or greater than about 10 milliwatts DC) from the channel 214 into the circuit 250 (i.e., at the initiation of a "Treatment Mode"), the SSR automatically switches the coil 120 into the current path of the channel 214, thereby allowing the coil 120 to heat to a therapeutic temperature level. When the delivery of the therapeutic power level is complete, the power supply can revert to delivering the relatively low power level. Upon re-initiation of the low power level, the SSR can automatically switch the coil 120 out of the current path of the channel 214, thereby re-initiating the Measure Mode and facilitating further use of the electrodes 124, 126 to determine location of the probe tip.

When an SSR is implemented in the circuit 250 shown in FIG. 8, upon initiation of the Treatment Mode, an AC voltage such as an RF voltage is applied between pin 1 and pin 2 of rectifier bridge D1. The rectification of the AC voltage results in a DC voltage between pin 3 and pin 4 of D1. This voltage charges capacitors C1 and C2 through R1. Resistor R1 limits the rate at which the capacitors are charged. C1 can be employed to prevent any high frequencies remaining after the rectification process from entering voltage regulator U1. D2, a zener diode, protects C2 and U1 from any voltage transients which may occur when an AC voltage such as an RF voltage is initiated. When the DC voltage at pin 2 of U1 reaches 3.1V, U1 output is regulated to 3.0V. R3 sets the drive current supplied to the LED of SSR1 to 3.0 mA, which exceeds the 2.0 mA threshold (by a 50% margin) that switches the photo-activated mosfet switch of SSR1. When Treatment Mode is halted and Measure Mode is resumed, R4 discharges C1 and C2 to reduce the input voltage to U1 to close to zero volts. With the input to U1 near zero volts, no LED drive voltage is present at SSR1 and therefore the mosfet switch of SSR1 is open, thereby switching the coil 120 out of the electrical path of the channel 214. The electrodes 124, 126 remain in the current path of the channel 214, and impedance/location sensing can resume.

The following chart summarizes component properties that can be used in one embodiment of the circuit 250:

| Item | Ref. | Part | Description | Size | Manufacturer |
| --- | --- | --- | --- | --- | --- |
| 1 | C1 | .1 uF | CAP .1UF 25 V CERAMIC XR7 | 0805 | Kemet |
| 2 | C2 | 10 uF | CAP TANTALUM 10UF 16 V 10% | 3528-21 | Kemet |

-continued

| Item | Ref. | Part | Description | Size | Manufacturer |
|---|---|---|---|---|---|
| 3 | D1 | CDBHD180L | DIODE SCHOTTKY 1 A 100 V | TO-269AA | Conchip Technology |
| 4 | D2 | 10 v | DIODE ZENER 350 MW 10 V 5% | SOT23-3 | Fairchild Semiconductor |
| 5 | R1 | 3.32k | RES 3.32K OHM 1/3 W .1% | 1210 | Vishay/Dale |
| 6 | R3 | 750 | RES 750 OHM 1/8 W .1% | 0805 | Panasonic - ECG |
| 7 | R4 | 20k | RES 20K OHM 1/8 W .1% | 0805 | Panasonic - ECG |
| 8 | SSR1 | PS710A | SSR OCMOS FET 2.0 A 1CH NO | 6-SMD | NEC |
| 9 | T1 | 9:1 | Trifilar, on .375" core; 9:1 | | VNUS |
| 10 | U1 | S812C30A | IC REG LDO 50 MA 3.0 V | SOT23-5 | Seiko Instruments |

Figure 9:
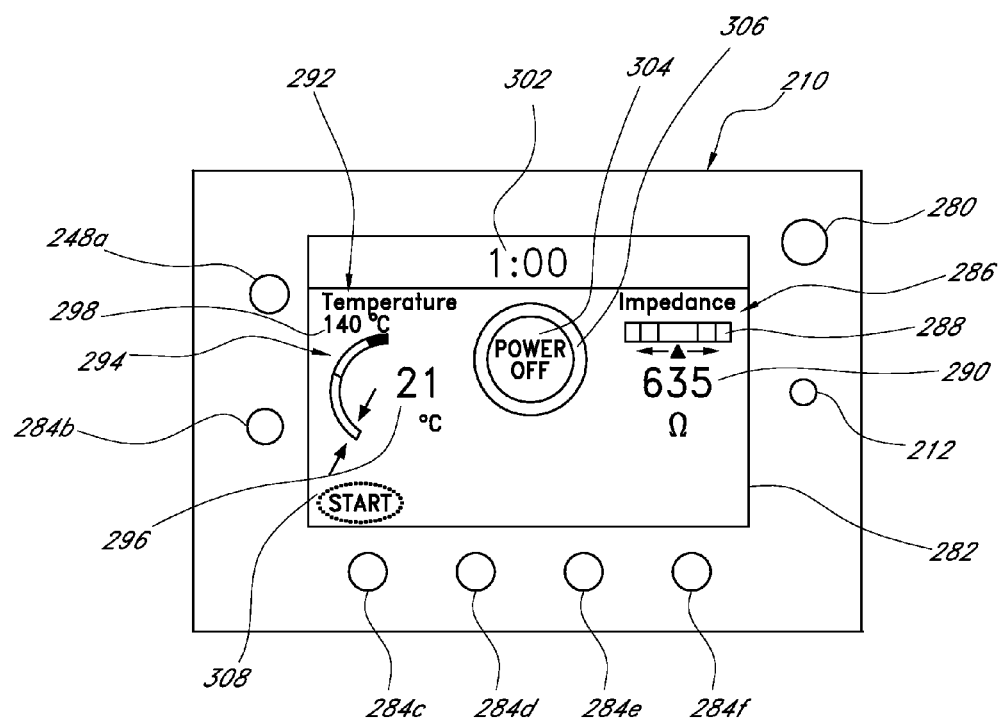
FIG. 9 is an elevation view of a user interface of the power supply of FIG. 1, when in a Measure Mode.
Figure 10:
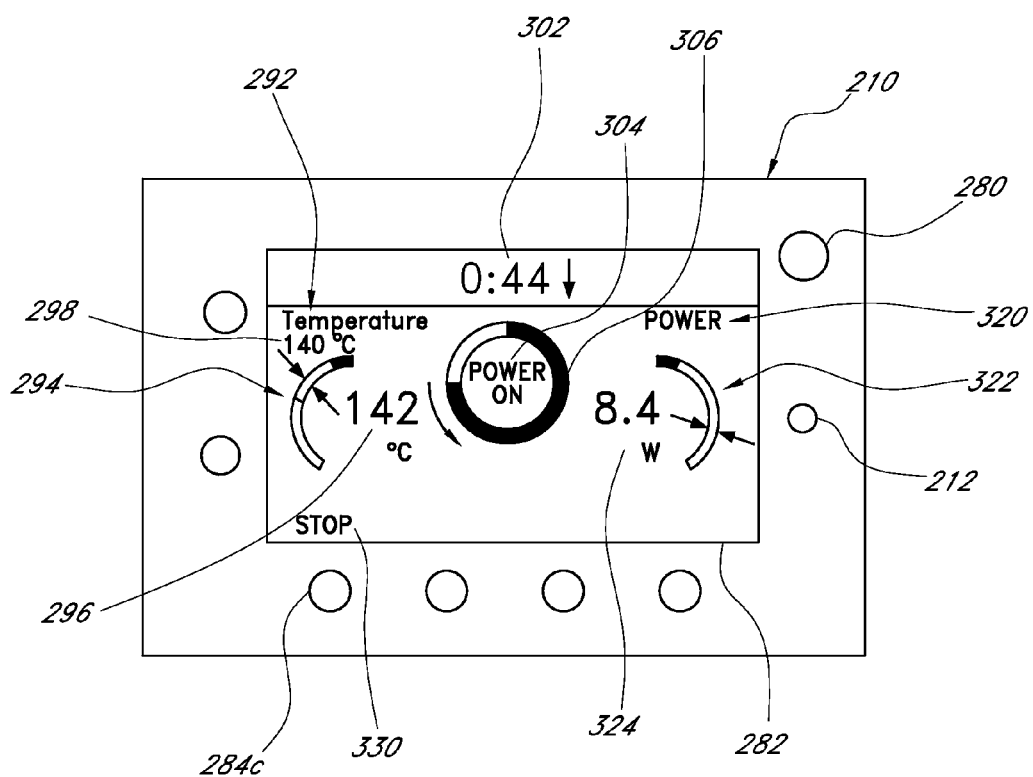
FIG. 10 is an elevation view of the user interface of FIG. 9, when in a Treatment Mode.

FIGS. 9 and 10 depict the operation of an embodiment of the power supply 210 in two operational modes of the treatment system 100 and probe 110: the Measure Mode which is depicted in FIG. 9, and the Treatment Mode which is depicted in FIG. 10.

The power supply 210 can comprise a user interface (aspects of which are depicted in FIGS. 9 and 10), a processor (not shown) and power generation circuitry (not shown). The power supply 210 can function under the control of the processor executing one or more algorithms or software stored in memory accessible by the processor. The user interacts with and sends commands and other input to the processor via the user interface, and the processor provides information and other output to the user via the user interface. While executing the software, the processor controls the functions of the power generation circuitry in response to commands and other input from the user, and/or sensor data received from the probe 110. The power generation circuitry outputs electrical power to the probe in the manner commanded by the processor. In addition to or instead of the above-described control architecture, the user interface can optionally support direct command of the power generation circuitry by the user, without participation by a processor. One example of a suitable power supply 210 is the RFGPlus™ radiofrequency generator (model no. RFG2) available from Covidien/VNUS Medical Technologies of San Jose, Calif. However any other suitable power supply, or any other suitable radiofrequency generator, may be used instead.

FIG. 9 depicts the user interface of the power supply 210 while in the Measure Mode. The user interface can include a device power button 280, display screen 282, and a number of control buttons 284a-f arranged along the edges of the display screen 282. The power supply 210 can be configured so that the control buttons 284a-f (or a subset thereof) function as "softkeys" wherein the function assigned to a given button 284 can be displayed on an adjacent portion of the display screen 282 whenever the function is available or in effect. Alternatively, some or all of the buttons 284a-f can have fixed functions, or be omitted altogether and the display screen 282 configured as a touchscreen.

The user can access the Measure Mode by plugging the connector 112 of the probe 110 into the socket 212, whereupon the power supply 210 recognizes the type of device that has been connected to the socket 212, e.g. by determining the resistance of an identification resistor located in the connector 112 or elsewhere in the probe 110. After confirming the connection of the probe 110, the power supply can load the portion(s) of software appropriate for operation of the probe 110 into memory for execution by the processor. The power supply 210 then illuminates or otherwise highlights (e.g. via the screen 282) the device power button 280. The user presses the device power button 280 to enable (but not yet initiate) delivery of a therapeutic level of power to the probe 110.

The power supply 210 enters the Measure Mode in response to the user pressing the device power button 280. In the Measure Mode, the power supply 210 can display appropriate information on the screen 282, e.g. as shown in FIG. 9. The screen 282 can include an impedance display 286, which can optionally include both an analog impedance gage 288 and a digital impedance gage 290. The digital gage 290 provides a precise numeric reading, whereas the analog gage 288 can indicate relative distance from an acceptable zone while providing rate-of-change information by virtue of the movement velocity of its pointer. The depicted example of an analog impedance gage 288 is in the form of a linear "slide rule" gage, with a central "green" zone, "yellow" zones immediately on either side thereof and "red" zones at the lateral extremities, and a laterally sliding pointer underneath. The screen 282 can also include a device temperature display 292, which can optionally include both an analog device temperature gage 294 and a digital device temperature gage 296. The depicted example of an analog temperature gage 294 is in the form of an arcuate gage, with a central "acceptable" zone, "too high" and "too low" zones immediately on either side thereof, and an angularly moving pointer next to the arcuately arranged zones. The temperature display 292 can also indicate the temperature setpoint 298 appropriate for the probe 110 or selected by the user. The screen 282 in the Measure Mode can also show (but not yet initiate) a digital treatment countdown timer 302, and display POWER OFF in a power status indicator 304, e.g. to indicate that a therapeutic level of power is not being delivered. The power status indicator 304 can be located inside an analog treatment countdown indicator 306, shown here in the form of a diminishing circle. Like the digital treatment countdown timer 302, the analog treatment countdown indicator 306 is not initiated during the Measure Mode.

During the Measure Mode, the power supply 210 delivers a relatively low, sub-therapeutic level of power (e.g. less than about 10 milliwatts RMS, or less than about 100 milliwatts peak; or less than about 10 milliwatts DC; or about 2.3 milliwatts RMS) to the probe 110 through the channel 214 (see FIG. 7). Because the power delivered during the Measure Mode is too low to close the switch 230, the Measure Mode power is directed through the electrodes 124, 126 alone. Thus, during Measure Mode, the user can manipulate the probe tip within the patient's body until the desired impedance level is reached, indicating that the probe is in contact with the desired medium (e.g. blood or a blood vessel wall). The user observes the impedance display 286 to determine the impedance sensed by the electrodes 124, 126.

When the sensed impedance reaches the acceptable level or range (which can be indicated in the central green zone, or the green and yellow zones, of the analog impedance gage 288), the power supply 210 can enable (but does not yet initiate) the delivery of a therapeutic level of power to the probe 110. Preferably, the power supply 210 does not enable therapeutic power delivery until acceptable level or range of impedance is reached. (Alternatively therapeutic power delivery can be enabled at any impedance level, leaving it entirely to the user's discretion when to initiate delivery of therapeutic power.) When therapeutic power delivery is enabled, the power supply 210 illuminates or highlights a START indicator 308 next to one of the control buttons 284c. The user presses the corresponding control button 284c to enter the Treatment Mode and initiate delivery of a therapeutic level of power (e.g. greater than about 10 milliwatts RMS, or greater than about 100 milliwatts peak; or greater than about 10 milliwatts DC) to the probe 110.

FIG. 10 depicts one example of the configuration of the power supply 210 during the Treatment Mode. The power status indicator 304 changes to POWER ON to indicate that a therapeutic power level is on and being delivered to the probe 110. The digital treatment countdown timer 302 and analog treatment countdown indicator 306 begin counting down to the end of the desired treatment period (e.g. at or about one minute). The analog indicator 306 displays a steadily diminishing arc which disappears at the twelve o'clock position upon termination of the treatment period. The temperature display 292 indicates the current device temperature (e.g. the coil temperature when the coil 120 is used to deliver therapeutic energy to the tissue under treatment) in both digital and analog forms. The analog gage 294 shows the current sensed temperature in relation to the endpoints of an acceptable temperature range. A power display 320 preferably replaces the impedance display 286, and comprises an analog power gage 322 and a digital power gage 324. The power display 320 indicates the current amount of power being delivered to the probe 110. The screen 282 displays a STOP label 330 next to one of the control buttons 284; preferably, the STOP label replaces the START label shown during the Measure Mode next to the same control button 284c. The STOP button enables the user to manually terminate delivery of therapeutic power to the probe 110.

Upon delivery of the therapeutic power level to the probe 110 via the channel 214 (see FIG. 7), the switch 230 closes, switching the coil 120 into the circuit coupled to the channel 214. Because of the relatively low impedance through the coil 120, the power passes almost entirely through the coil 120, heating the coil sufficiently for treating nearby tissue. Optionally, the probe 110 or power supply 210 can be configured to diminish or terminate altogether any power delivered to the electrodes 124, 126 during Treatment Mode.

At the conclusion of the full treatment period (or upon manual termination of the therapeutic power delivery) the power supply 210 terminates the Treatment Mode and preferably resumes the above-described Measure Mode. The power supply resumes delivery of sub-therapeutic power through the channel 214, and in response the switch 230 re-opens, switching the coil 120 back out of the circuit coupled to the channel 214. From the resumed Measure Mode the user can employ impedance sensing again to position the probe tip in another desired treatment location, and re-initiate the Treatment Mode to deliver another treatment to the targeted tissue.

Figure 11:
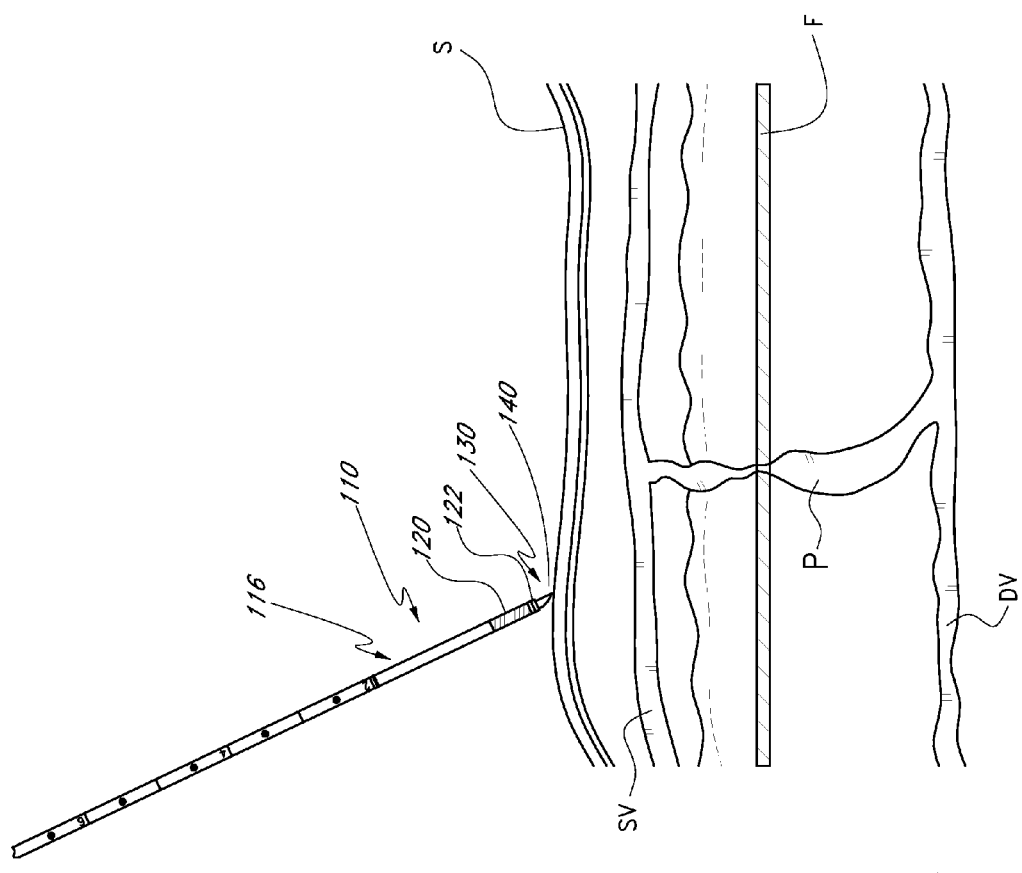
FIG. 11 is a partial sectional view of a method of using the probe of FIG. 1 to treat a perforator vein.
Figure 12:
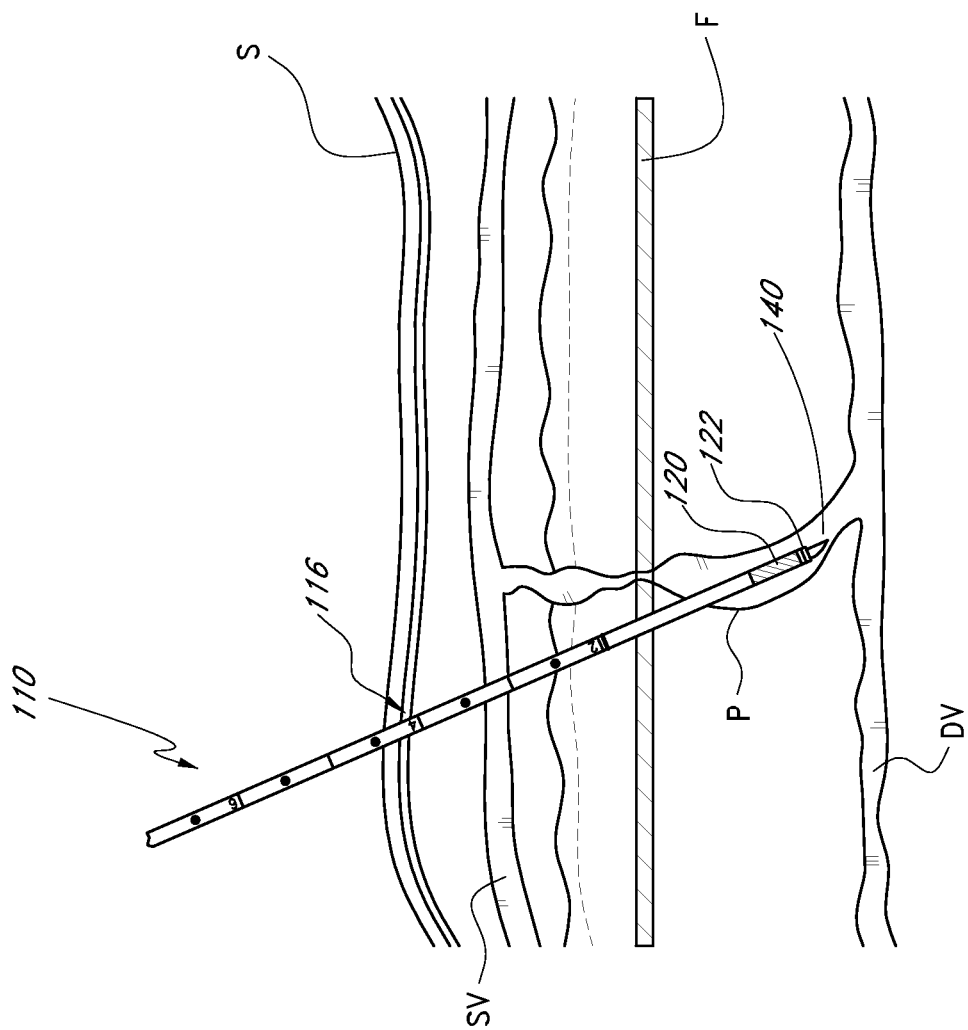
FIG. 12 is another partial sectional view of the method of FIG. 11.

FIGS. 11-15 depict one example of a method of using a device such as the probe 110 (e.g., any embodiment of the probe 110 disclosed herein, or any other suitable device) to treat a perforator vein P, or other HAS. In the depicted anatomy, the skin surface S overlies a superficial vein SV which is connected via the perforator vein P to a deep vein DV. From the superficial vein SV, the perforator vein P extends through a layer of fascia F and/or other intervening tissues before reaching the deep vein DV. Access to the perforator vein P can be achieved using a "direct access" approach wherein the sharp distal tip 140 of the needle 130 is urged against the skin surface S, puncturing the skin and enabling the probe shaft 116 to penetrate through the overlying tissue (including, e.g., the fascia F) and into the lumen of the perforator vein P. The probe shaft 116 thus reaches the position shown in FIG. 12, with the coil 120 and electrodes 122 inside the lumen of the perforator vein P. Alternatively, an "over-the-wire" approach can be employed to access the perforator vein P. In such a technique, the needle 130 is removed from the probe 110, and a hollow access needle (not shown) is inserted through the skin surface S and into the perforator vein P. A guidewire (not shown) is inserted through the access needle until a distal portion of the guidewire extends into the perforator vein. The access needle is then withdrawn over the guidewire, leaving the distal guidewire in the vein and the proximal guidewire extending out of the access site past the skin surface S. The proximal guidewire is then inserted through the lumen 128 of the probe shaft 116, and the probe shaft 116 is inserted over the guidewire through the tissue tract formed by the access needle and into the perforator vein P. As a result the probe shaft 116 is positioned in the anatomy as shown in FIG. 12 (but without the needle tip 140 present), with the coil 120 and electrodes 122 inside the lumen of the perforator vein P.

During the insertion process shown in FIGS. 11 and 12, a handheld ultrasound probe (not shown) can optionally be used to guide the insertion of the probe 110. Instead of or in addition to the ultrasound probe, the electrodes 122 can be used to position the probe 110 where desired in the anatomy. When using the electrodes 122 in such a manner, the power supply 210 is placed in the Measure Mode before or during insertion of the probe 110. The electrodes 122 thus sense the impedance of the tissue(s) with which the electrodes are in contact as the user moves the probe shaft 116 toward the perforator vein, and the power supply 210 receives and displays the sensed impedance information. The user can observe the sensed impedance on the screen 282 (see, e.g., FIG. 9) and thereby determine the type of tissue in contact with the electrodes, or determine simply whether or not the electrodes are in contact with the desired tissue type (e.g. blood or perforator vein wall). By appropriately maneuvering the probe shaft 116 in the patient's anatomy and observing the sensed impedance, the user positions the tip of the shaft 116 in the lumen of the perforator vein P (see, e.g., FIG. 12). The user determines that the tip of the shaft 116 is in the desired location in the perforator vein P when he or she observes the desired impedance reading on the screen 282. The desired impedance reading results from the electrodes 122 being in contact with and/or positioned in the desired tissue type and the electrodes sensing the impedance that is characteristic of that tissue type (or an impedance that is within an impedance range that is characteristic of that tissue type). The power supply 210 displays this characteristic impedance sensed by the electrodes 122.

Upon reaching the desired position of the probe tip, the user can optionally confirm the position of the probe tip via ultrasound and/or impedance sensing, and/or perform final adjustments of the probe tip guided by ultrasound and/or impedance sensing. If present, the needle 130 is then removed from the probe shaft 116. Following confirmation that the electrodes are within the vein P, the user can advance the probe 110 approximately 0.5 cm to ensure that the coil 120 is inside the vessel to be treated. Tumescent anesthetic fluid (or any suitable local anesthetic can then optionally be injected into the perivenous space surrounding the perforator vein P, and/or manual compression can be applied at the skin surface S via an ultrasound probe, tourniquet, pressure cuff, etc. Any combination of these techniques can optionally be employed to compress the perforator vein wall toward or into apposition with the coil 120, and/or exsanguinate the vein P. In addition, the patient can be placed in the Trendelenberg position (with the legs above the heart) to exsanguinate the vein P.

Local anesthetic can also be injected into the tissue near the portion of the vein P to be treated, in order to create 0.5 cm or more of separation between the proximal end of the coil 120 and the skin, and between the distal tip of the probe 110 and the deep venous system. The user can confirm via ultrasound or other visualization that the distal tip of the probe 110 is at least 0.5 cm from the deep venous system, and that the proximal end of the coil 120 is at least 0.5 cm from the skin.

The user then starts the delivery of electrical power at a therapeutic power level into the coil 120. For example, the user can press the START button on the power supply 210 (see FIG. 9), which causes the power supply 210 to end the Measure Mode and enter the Treatment Mode (see FIG. 10). Upon delivery of the higher, therapeutic power level to the probe 110 via the channel 214 (see FIG. 7), the switch 230 closes, switching the coil 120 into the circuit coupled to the channel 214. Because of the relatively low impedance through the coil 120, the power passes almost entirely through the coil 120, heating the coil sufficiently for treating the adjacent wall of the perforator vein P. In this manner the coil 120 is heated to a desired temperature and that temperature is maintained for a desired treatment period. The desired treatment temperature can optionally be at or about 140 degrees Celsius, and the treatment period can optionally be at or about one minute. Alternatively, the treatment temperature can be between 70 and 200 degrees Celsius, or between 120 and 160 degrees Celsius, and the treatment period can be varied above or below one minute to achieve the desired therapeutic effect.

Figure 13:
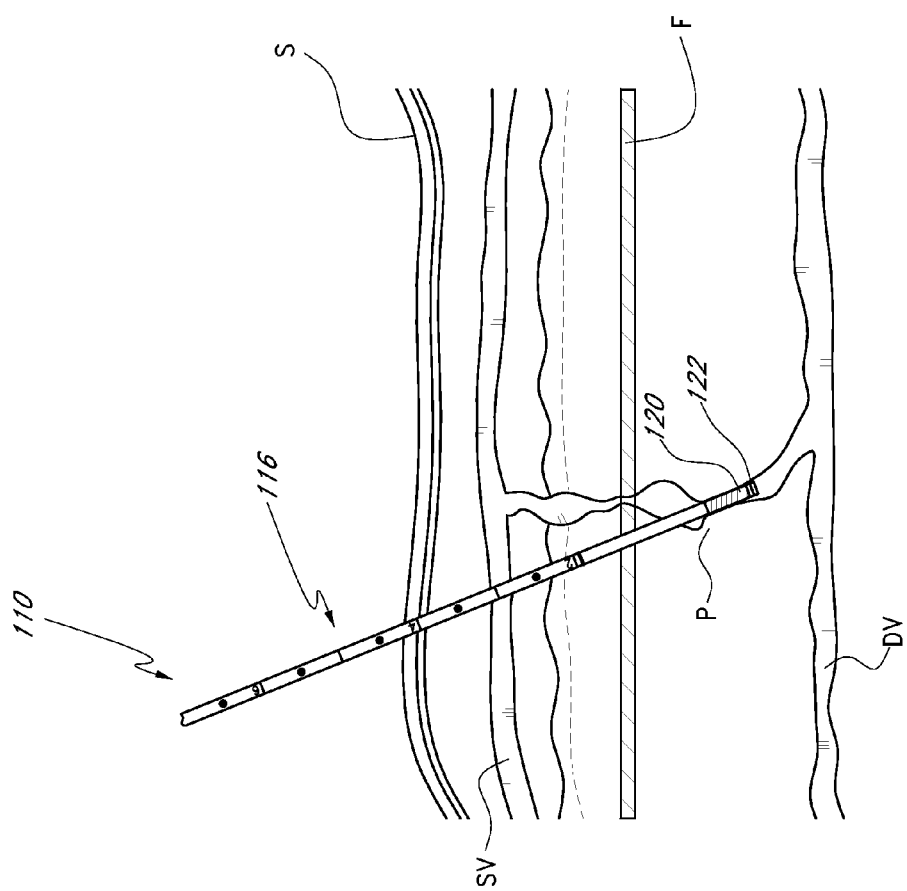
FIG. 13 is another partial sectional view of the method of FIGS. 11-12.

The probe 110 applies heat to the wall of the perforator vein P during the treatment period, which causes the vein wall to heat up in response and to shrink around the coil 120, as shown in FIG. 13. Thus the probe 110 forms a first constriction CON1 (see FIG. 14) in the perforator vein P.

At the conclusion of the treatment period, the power supply 210 terminates the Treatment Mode and preferably resumes the above-described Measure Mode. The power supply resumes delivery of sub-therapeutic power through the channel 214, and in response the switch 230 re-opens, switching the coil 120 back out of the circuit coupled to the channel 214.

Figure 14:
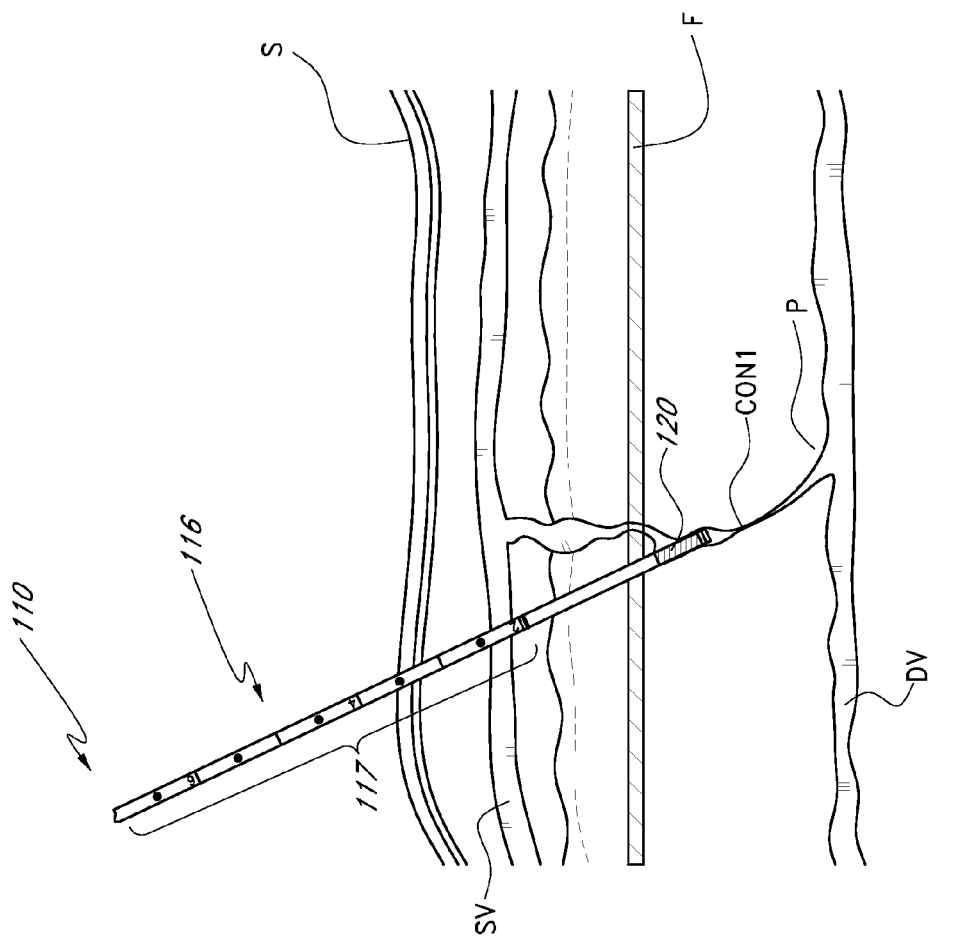
FIG. 14 is another partial sectional view of the method of FIGS. 11-13.
Figure 15:
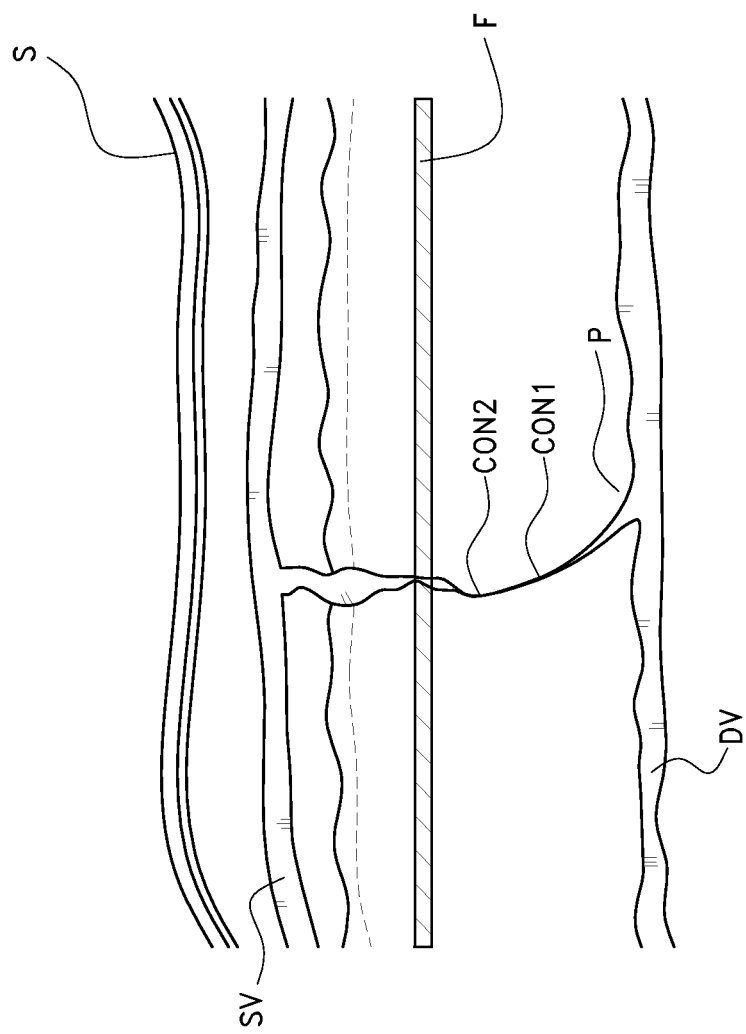
FIG. 15 is another partial sectional view of the method of FIGS. 11-14.

After forming the first constriction CON1, the user can withdraw the probe 110 from the patient altogether and cease treatment, or the user can withdraw the probe 110 proximally within the perforator vein P to a new position as shown in FIG. 14, where the entire coil 120 is located adjacent to, or the coil 120 extends slightly into (e.g. overlaps with), the first constriction CON1. (Also, if desired, the treatment cycle may be repeated in the vein segment just treated.) While the user withdraws the probe 110 proximally in this manner, the power supply 210 is in Measure Mode and impedance sensing can be employed as described above to ensure that the probe tip is placed in or remains in the perforator vein P.

Instead of or in addition to the use of impedance sensing, markings 117 on the outside of the shaft 116 can be employed to determine the distance (e.g. desirably about 5 mm) by which the coil 120 has been withdrawn proximally. The markings 117 can include numbered markings at one-centimeter intervals, and half-centimeter markings midway between adjacent numbered or whole-centimeter markings. Ultrasound can also be employed to determine or confirm that the probe tip is positioned properly within the perforator vein P for additional treatment thereof, and determine whether any residual blood flow exists following the first treatment cycle.

The user can then once again start the delivery of electrical power at a therapeutic power level into the coil 120, and perform a second treatment cycle similar to the one performed to form the first constriction CON1. At the conclusion of the second treatment cycle, a second constriction CON2 (FIG. 15) has been formed in the perforator vein P, and the second constriction CON2 preferably overlaps with or is adjacent or otherwise contiguous with the first constriction CON1. After the second treatment cycle, the probe 110 can be re-positioned again in the perforator vein P to perform an additional treatment in a manner similar to that described above, or the probe 110 can be withdrawn from the patient altogether to end the procedure.

At the conclusion of the second treatment period, the power supply 210 terminates the Treatment Mode and preferably resumes the above-described Measure Mode. The power supply resumes delivery of sub-therapeutic power through the channel 214, and in response the switch 230 re-opens, switching the coil 120 back out of the circuit coupled to the channel 214. If the second treatment cycle/period is the last one performed, the power supply can remain in Measure Mode until shutdown or an additional procedure is performed at another location in the patient.

Following treatment the patient can be instructed to ambulate frequently, not sit or stand for long periods of time and to avoid strenuous activity or lifting for up to five days. Compression should be employed over the treatment site as well. A follow-up examination can be performed within 72 hours to ensure that there is no thrombus extension into non-targeted vessels, including the deep venous system.

Figure 16:
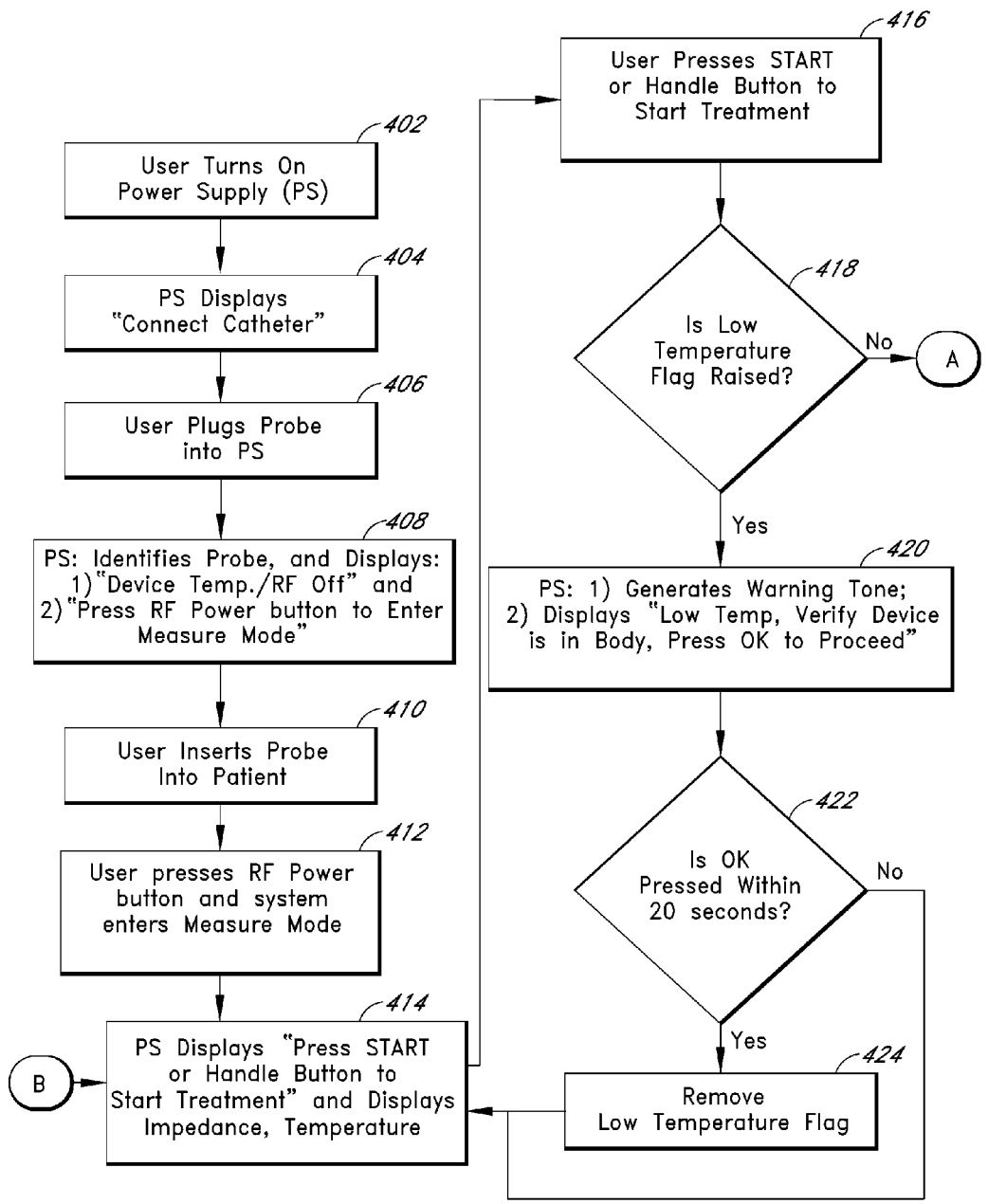
FIG. 16 is a flowchart illustrating part of an algorithm for use with and/or execution by the probe and power supply of FIG. 1.
Figure 17:
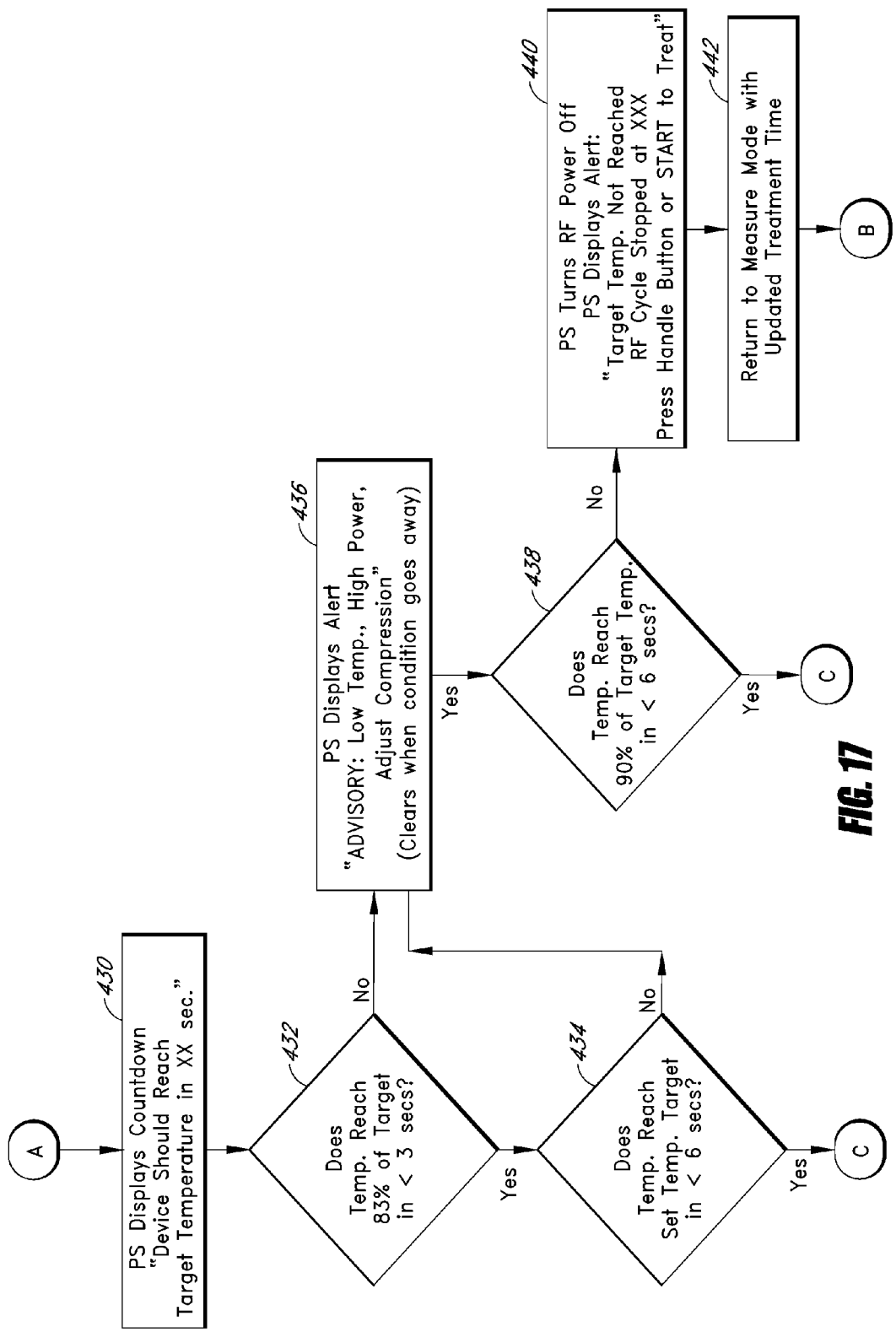
FIG. 17 is a flowchart illustrating another part of the algorithm of FIG. 16.
Figure 18:
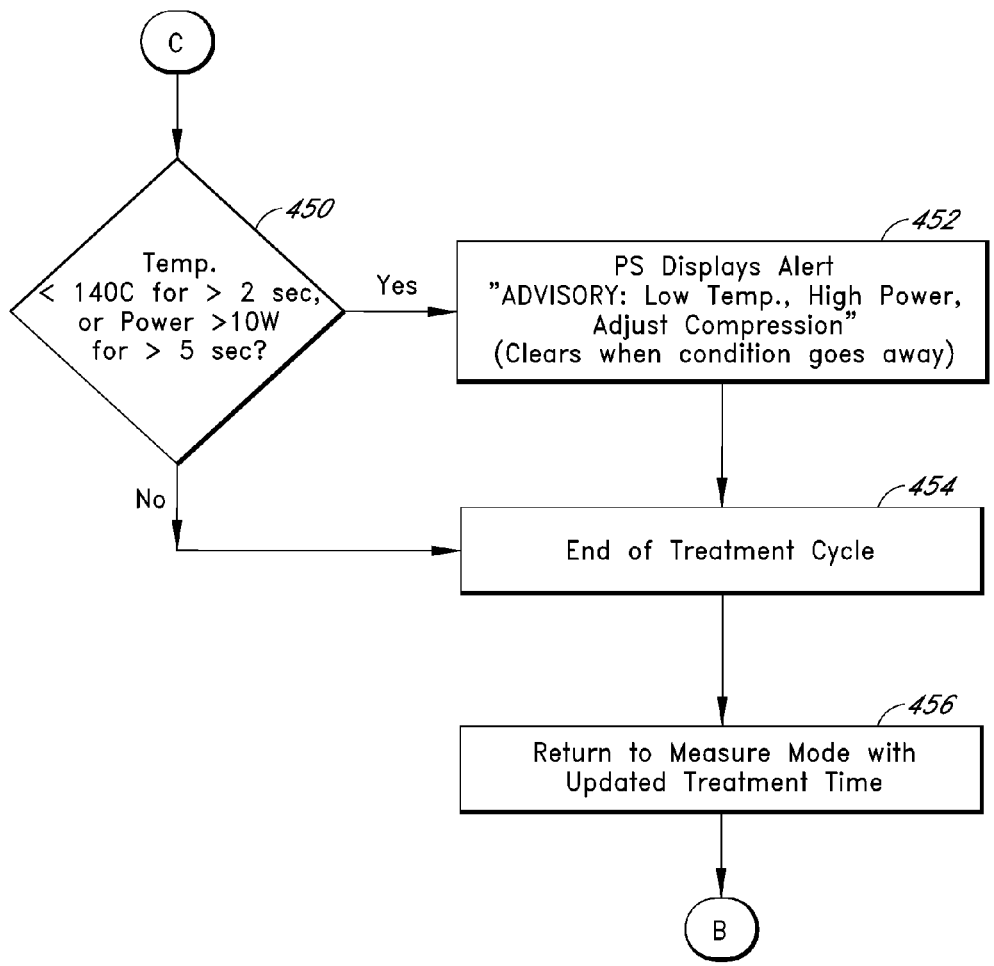
FIG. 18 is a flowchart illustrating another part of the algorithm of FIGS. 16-17.

FIGS. 16-18 depict one embodiment of an algorithm for operation of the system 100 with the probe 110 and the power supply 210. However, any other suitable algorithm may be employed in the use of the system 100, and the depicted algorithm(s) can be used with any suitable device and power supply other than the probe 110 and power supply 210.

FIG. 16 depicts the initial set-up of the system 100. First, the user turns on the power supply (Block 402). The power supply 210 ("PS") then displays a prompt for the user to connect the probe 110 to power supply 210 (Block 404). The user then plugs the connector 112 into the power supply 210 (Block 406).

In Block 408, the power supply 210 identifies the model of the device just plugged in and provides a display prompt indicating that the system is ready to be used. When the probe 110 is plugged into the power supply 210, the power supply can optionally determine a device ID, which can be set by a predetermined resistance value in the connector 112. The power supply 210 then loads software appropriate for the identified device. The loaded software can contain algorithms for operating the system's user interface and controlling output of electrical power (e.g., radio frequency (RF) power) by the power supply 210 to the probe 110. The display 282 can show the user a temperature reading from the temperature sensor 162, and/or an impedance reading from the electrodes 122.

The user then inserts the shaft 116 of the probe 110 into the patient (Block 410), and in response to a prompt from the power supply 210 presses the device power button 280 (e.g. an "RF Power" button). In response, the power supply 210 and the system 110 enter the Measure Mode discussed above. The user then navigates the probe tip to the desired treatment location (e.g., within a target blood vessel, such as a perforator vein, or other HAS) using the information provided by the power supply 210 in the Measure Mode (see, e.g., FIGS. 9, 11-15 and associated description herein).

During Measure Mode, the power supply 210 can also display (Block 414) a prompt to the user to press the START button on the power supply 210 as shown in FIG. 9, or a button (not shown) on the handle 118 of the probe 110 or elsewhere on the probe 110, to start the delivery of therapeutic power (e.g. a relatively high level of RF power) to the probe 110. In Block 416, the user presses the START button or the probe handle button to initiate delivery of therapeutic power.

Upon receiving the command from the user to initiate delivery of therapeutic power, the power supply 210 performs a temperature check (Block 418) based on the temperature information provided by the temperature sensor 162. If a low temperature is not sensed (e.g. if a low temperature "flag" is not raised), the system 100 continues with the Treatment Mode and proceeds to the algorithm shown in FIGS. 17-18. If the sensed temperature is too low, as can result from the probe tip not being within the patient, then the power supply 210 can execute a correction routine as shown in Blocks 420-424. In Block 420, the power supply can sound a warning tone and/or display a warning and a request to the user to confirm that the probe tip is in the body, and if so to press the "OK" button. If the user presses the OK button within 20 seconds (Block 422), then the low temperature flag is removed (Block 424), and the system returns to the Measure Mode (Block 414) with the low temperature flag removed. If the user does not press the OK button within 20 seconds, then the low temperature flag is not removed, and the system returns to the Measure Mode (Block 414) with the low temperature flag still raised.

Instead of or in addition to the temperature check described above, the system 100 can perform an impedance check by sensing the impedance across the electrodes 122. If the sensed impedance is higher than that expected of bodily tissue in contact with the electrodes 122, then delivery of therapeutic power can be prevented until a "high impedance" flag is lowered. Such an impedance check can otherwise proceed in a manner similar to that shown in Blocks 418-424 and described above in the context of a low temperature flag.

Upon proceeding to the algorithm shown in FIG. 17, the power supply 210 begins with a powerup monitoring routine shown in Blocks 430-442. In Block 430, the power supply 210 begins delivering power (e.g. radiofrequency energy, at a fundamental frequency of 460 kHz) to the probe 110 and displays a message (Block 430) indicating that treatment has started and provides a countdown to the time limit during which the target temperature of the coil 120 (sensed by the temperature sensor 160) should be met.

Blocks 432 and 434 are tests to ensure that the target temperature of the coil 120 is being approached with sufficient speed, i.e. that the coil 120 is heating up quickly enough. If either of these tests fail, then an advisory alert is provided to the user (Block 436) and the user is requested to adjust the compression applied to the treatment site, and/or to adjust the position of the probe tip in the patient's anatomy. In Block 438 a second-stage temperature test is performed to determine if the coil 120 is heating up quickly enough, this time with a slightly lower minimum heatup rate than required in Blocks 432 and/or 434.

If none of the tests of Blocks 432, 434, or 438 are passed, then the Treatment Mode is terminated. In Blocks 440 and 442 the therapeutic power is turned off and the user is prompted to press the appropriate control to restart treatment, while the system returns to Measure Mode and reports an updated cumulative treatment time (Block 442). Accordingly the system returns to Block 414 (FIG. 16).

If any of the tests of Blocks 432, 434, or 438 are passed, then the system 100 can proceed to the next step of treatment, as shown in FIG. 18. The power supply 210 can execute a power delivery monitoring routine shown in Blocks 450-454. In Block 450 the power supply 210 tests to ensure that coil temperature (and/or power delivered) remain above a predetermined minimum level (or below a predetermined maximum level) for predetermined minimum time periods. If not, the user is requested to adjust compression applied to the treatment site (Block 452), and/or to adjust the position of the probe tip in the patient's anatomy. If so, the treatment (including the delivery of power to the probe 110 at a therapeutic level) proceeds until completion (Block 454) which occurs when the desired treatment period (e.g. at or about one minute) has elapsed. The system 100 then returns to the Measure Mode and the power supply 210 reports an updated cumulative treatment time in the display 282 of FIG. 9 (Block 456). Accordingly, the process cycles back to Block 414.

In one embodiment, power delivery in Treatment Mode begins at 30 watts and drops to below 10 watts within 10 seconds if compression is applied properly to the coil 120 within the vein P, the vein P has been properly exsanguinated, and the coil 120 is properly positioned. If the set temperature is not reached within 5 seconds after the commencement of energy delivery, or if the power level is maintained above 10 watts, there may be remaining blood flow within the vein that cools the treatment segment. The tests implemented in the algorithm ensure that the desired power delivery parameters are achieved.

The system 100 can optionally sense and monitor impedance across the electrodes 122 during the Treatment Mode (e.g. while executing the algorithms of FIGS. 17 and 18). If the sensed impedance at any point during the Treatment Mode exceeds a maximum value associated with or expected of bodily tissue in contact with the electrodes 122 (as can occur if the probe tip is removed from the patient altogether), the system can terminate the Treatment Mode and the delivery of therapeutic power to the coil 120. This can provide a safety measure by preventing power-up or further delivery of therapeutic power to the coil 120 when the probe tip is outside the patient's tissue. For example, the system 100 can execute this impedance monitoring routine along with the temperature/power tests of Blocks 432, 434, 438 and 450. The above-described maximum impedance value can be considered a functional impedance limit of the system 100.

The algorithms described above in connection with FIGS. 16-18 can be implemented as program instructions or software stored in memory accessible to the processor of the power supply 210. The processor can access and execute the program instructions to operate the system 100 according to the algorithms of FIGS. 16-18.

Despite the foregoing discussion of certain embodiments, only the following claims, and such other claims as may be presented in the future based on the disclosure herein (and not the present Detailed Description), are intended to define the invention(s) protected hereby.

What is claimed is:

1. Apparatus for performing therapy on tissue, the apparatus comprising:
    an elongate shaft having a distal portion configured for insertion into a hollow anatomical structure (HAS);
    a power lead;
    a sensor located at the shaft distal portion and configured to receive power through the power lead at a relatively low sensing level to determine which medium the sensor is in contact with;
    a therapeutic energy application device located at the shaft distal portion and configured to selectively receive power through the power lead at a relatively high treatment level; and
    a switch including an open position and a closed position;
    wherein the sensor is electrically connected to the power lead, and the therapeutic energy application device is electrically connected to the power lead only when the switch is in the closed position; and
    wherein the switch is in the open position when power is received through the power lead at the sensing level, and the switch automatically closes to electrically apparatus of connect the energy application device to the power lead in response to power being received through the power lead at a level above the sensing level.

2. The apparatus of claim 1, wherein the sensing power level is less than about 10 mW.

3. The apparatus of claim 1, wherein the switch is a diode for alternating current (DIAC).

4. The apparatus of claim 1, wherein the switch is a triode for alternating current (TRIAC).

5. The apparatus of claim 1, wherein the switch is photo-activated.

6. The apparatus of claim 1, wherein the switch is a solid-state relay.

7. The apparatus of claim 1, wherein the sensor comprises a pair of electrodes.

8. The apparatus of claim 1, wherein the energy application device comprises an electrically driven heating element that is electrically insulated from any adjacent tissue.

9. The apparatus of claim 1, wherein the power lead is configured to be connected to a first output channel of a power supply.

10. The apparatus of claim 9, wherein the sensor is electrically connected to the power supply upon connection of the power lead to the first output channel.

11. The apparatus of claim 9, wherein the energy application device is electrically connected to the power supply upon connection of the power lead to the first output channel and closure of the switch.

* * * * *